(12) United States Patent
Bourrie et al.

(10) Patent No.: US 7,893,259 B2
(45) Date of Patent: Feb. 22, 2011

(54) PYRIDO-PYRIMIDINE DERIVATIVES, PREPARATION THEREOF, AND THERAPEUTIC USE THEREOF

(75) Inventors: Bernard Bourrie, Saint-Gely-du-Fesc (FR); Pierre Casellas, Montpellier (FR); Samir Jegham, Montferrier-sur-Lez (FR); Pierre Perreaut, Saint-Clement-de-Riviere (FR)

(73) Assignee: Sanofi-Aventis, Paris (FR)

( * ) Notice: Subject to any disclaimer, the term of this patent is extended or adjusted under 35 U.S.C. 154(b) by 10 days.

(21) Appl. No.: 12/415,256

(22) Filed: Mar. 31, 2009

(65) Prior Publication Data

US 2009/0233923 A1 Sep. 17, 2009

Related U.S. Application Data

(63) Continuation of application No. 11/651,376, filed on Jan. 8, 2007, now Pat. No. 7,544,682, which is a continuation of application No. PCT/FR2005/001809, filed on Jul. 13, 2005.

(30) Foreign Application Priority Data

Jul. 15, 2004  (FR) .................................. 04 07898

(51) Int. Cl.
C07D 471/04 (2006.01)
A61P 35/00 (2006.01)
A61P 35/02 (2006.01)
(52) U.S. Cl. .................................................. 544/279
(58) Field of Classification Search .................. 544/279
See application file for complete search history.

(56) References Cited

U.S. PATENT DOCUMENTS

| 3,534,039 A | 10/1970 | Davoll |
| 5,620,981 A | 4/1997 | Blankley et al. |
| 5,733,913 A | 3/1998 | Blankley et al. |
| 5,733,914 A | 3/1998 | Blankley et al. |
| 5,952,342 A | 9/1999 | Blankley et al. |
| 7,504,406 B2 | 3/2009 | Bourrie |
| 7,714,151 B2 * | 5/2010 | Kelly et al. .............. 549/404 |
| 2009/0233923 A1 * | 9/2009 | Bourrie et al. ........... 514/234.2 |

FOREIGN PATENT DOCUMENTS

| EP | 0 790 997 B1 | 3/2000 |
| WO | WO 96/15128 | 5/1996 |
| WO | WO 96/34867 | 11/1996 |
| WO | WO 01/21577 A2 | 3/2001 |
| WO | WO 01/55147 | 8/2001 |
| WO | WO 01/70741 A1 | 9/2001 |
| WO | WO 02/12238 A2 | 2/2002 |
| WO | WO 03/000011 | 1/2003 |
| WO | WO 2004/063195 A1 | 7/2004 |
| WO | WO 2004/085436 | 10/2004 |
| WO | WO 2005/105097 A2 | 11/2005 |
| WO | WO 2007/003765 | 1/2007 |
| WO | WO 2007/080324 A3 | 7/2007 |

OTHER PUBLICATIONS

U.S. Appl. No. 12/166,431, filed Jul. 2, 2008, Perreaut.
Alam, Fighting Cancer: 'Magic Bullets' on Target to Lead Market, Pharmalicensing.com (Mar. 8, 2005).
Albrecht, Untersuchungen uber die antibakterielle Aktivitat von Chinoloncarbonsauren. VI (1). Der Einfluss von kondensierten Funfringen und 1-Substituenten, Eur. J. Med. Chem.-Chimica Therapeutica, 1977 (12) 3 pp. 231-235.
Antoine et al, Acides m-dioxino quinoleine carboxyliques a action antibacterienne. II., Chimie Therapeutique, 1972 (7) 6 pp. 443-449.
Anzali et al, 1. Endothelin antagonists: Search for Surrogates of Methylendioxyphenyl by Means of a Kohonen Neural Network, Bioorganic & Medicinal Chemistry Letters 8 (1998) pp. 11-16.
Ariza et al, Bocdene and Mocdene Derivatives of Catechols and Catecholamines, Oragnic Letters, 2001 (3) 9 pp. 1399-1401.
Cambie et al, Towards the synthesis of aminodibenzo[b,e][1,4]dioxin derivatives via cationic ruthenium complexes, J. Organo. Chem., 1996 (507) pp. 1-21.
Carmichael et al, Evaluation of a Tetrazolium-based Semiautomated Colorimetric Assay: Assessment of Chemosensitivity Testing, Cancer Research, 1987 (47) pp. 936-942.
Clark et al, Synthesis and Analgesic Activity of 1,3-Dihydro-3-(substituted phenyl)imidazo[4,5-b]pyridin-2-ones and 3-(Substituted phenyl)-1,2,3-triazolo[4,5-b]pyridines, J. Med. Chem., 1978 (21) 9 pp. 965-978.

(Continued)

Primary Examiner—James O Wilson
Assistant Examiner—Cecilia M Jaisle
(74) Attorney, Agent, or Firm—Scully, Scott, Murphy & Presser, P.C.

(57) ABSTRACT

The disclosure concerns pyrido[2,3-d]pyrimidine derivatives, their preparation and their therapeutic application, of general formula (I):

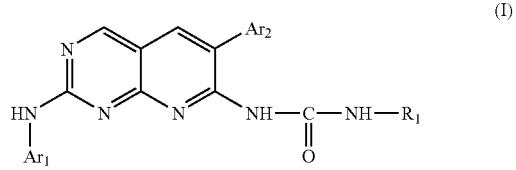

and acid addition salts, hydrates and solvates thereof, as well as in the form of enantiomers, diastereoisomers and mixtures thereof. The disclosure also concerns methods for preparing said derivatives, pharmaceutical compositions containing a compound of general formula (I), and their therapeutic use.

8 Claims, No Drawings

OTHER PUBLICATIONS

Colomb et al, Nuclear Texture Parameters as Discriminant Factors in Cell Cycle and Drug Sensitivity Studies, Cytometry, 1991 (12) pp. 15-25.

Drexler, Leukemia Cell Lines: in vitro Models for the Study of Chronic Myeloid Leukemia, Leukemia Research, 1994 (12) 12 pp. 919-927.

El Hadri et al, New Series of N-substituted Phenyl Ketone Oxime Ethers: Synthesis and Bovine Beta3-adrenergic Agonistic Activities, Pharmazie, 2003 (58) pp. 13-17.

Fujishita, et al, Sensitivity of Non-Small-Cell Lung Cancer Cell Lines Established from Patients Treated with Prolonged Infusions of Paclitaxel, Oncology, 2003 (64) pp. 399-406.

Kuriyama et al, CLM-T1: A Cell Line Derived From T-Lymphocyte Acute Phase of Chronic Myelogenous Leukemia, Blood, 1989 (74) 4 pp. 1381-1387.

Lewell et al, Drug Rings Database with Web Interface. A Tool for Identifying Alternative Chemical Rings in Lead Discovery Programs, J. Med. Che. 2003, 46, pp. 3257-3274.

Mederski et al, 2. Endothelin Antagonists: Evaluation of 2,1,3-Benzothiadiazole as a Methylendioxyphenyl Bioisoster, Bioorganic & Medicinal Chemistry Letters 8 (1998) pp. 17-22.

Nakai et al, New Potent Antagonists of Leukotrienes C4 and D4. 1. Synthesis and Structure-Activity Relationships, J. Med. Chem., 1988 (31) pp. 84-91.

Palmer et al, Structure-activity Relationships for 2-anilino-6-phenylpyrido[2,3-d]pyrimidin-7(8H)-ones as Inhibitors of the Cellular Checkpoint Kinase Wee1, Bioorganic & Medicinal Chemistry Letters 15 (2005) pp. 1931-1935.

Schroeder et al, Soluble 2-Substituted Aminopyrido[2,3-d]primidin-7-yl Ureas. Structure—Activity Relationships against Selected Tyrosine Kinases and Exploration of in Vitro and in Vivo Anticancer Activity, J. Med. Chem., 2001, 44, 1915-1926.

Sicinski, Killer Breast Cancer Therapy Hope, BBC News/Health Jan. 21, 2006.

Soda et al, Lymphoid Crisis with T-cell Phenotypes in a Patient with Philadelphia Chromosome Negative Chronic Myeloid Leukaemia, British Journal of Haematology, 1985 (59) pp. 671-679.

Thompson et al, Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receiptor-1 and Vascular Endothelial Growth Factor Receptor-2 Tyrosine Kinases, J. Med. Chem., 2005,48, 4628-4653.

Walsh, No 'Magic Bullet' Cure for Cancer, BBC News, International Version, Medical Notes, Feb. 1, 2007.

Westphal et al, Epidermal Growth Factor Receptors in the Human Glioblastoma Cell Line SF268 Differ From Those in Epidermoid Carcinoma Cell Line A431, Biochemical and Biophysical Research Comm., 1985 (132) 1 pp. 284-289.

Yeh et al, Syntheses of 6-Amino-1,3-benzodioxin and Its p-Arylazo-Substituted Calix[4]arenes, J. Org. Chem., 1994 (59) pp. 754-757.

* cited by examiner

PYRIDO-PYRIMIDINE DERIVATIVES, PREPARATION THEREOF, AND THERAPEUTIC USE THEREOF

This application is continuation of U.S. patent application Ser. No. 11/651,376, filed Jan. 8, 2007, now allowed, which is a continuation of International Application No. PCT/FR2005/001809, filed Jul. 13, 2005, which are incorporated herein by reference in their entirety; which claim the benefit of priority of French Patent Application No. 0407898, filed Jul. 15, 2004.

The present invention relates to pyrido[2,3-d]pyrimidine derivatives, to their preparation and to their therapeutic application.

Compounds derived from pyrido[2,3-d]pyrimidine have been described in International patent applications WO 01/55147 and WO 03/000011 and in European and United States patents EP-B-790 997 and U.S. Pat. No. 5,733,913 respectively. Those compounds are of potential use in treating cellular proliferation disorders.

In a first aspect, the present invention concerns compounds of formula (I):

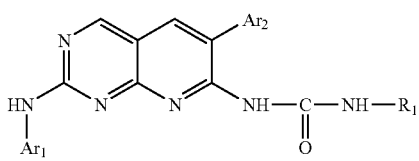

in which:

$R_1$ is selected from the group constituted by $(C_1-C_6)$alkyl, $(C_3-C_7)$cycloalkyl, $CH_2COR_4$, phenyl or phenyl substituted with hydroxyl and/or halogen and/or $(C_1-C_6)$alkyl;

$R_4$ represents a hydroxyl, $(C_1-C_4)$alkoxy, amino, $(C_1-C_4)$alkylamino or di$(C_1-C_4)$alkylamino group;

$Ar_1$ represents a radical selected from:

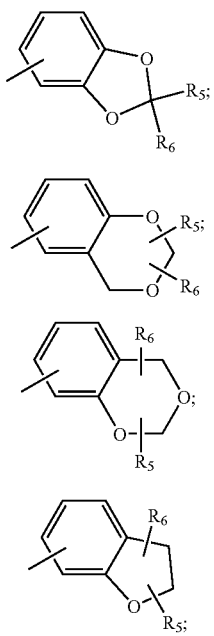

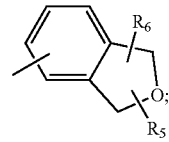

$R_5$ represents a cyano, hydroxy(C1-C4)alkyl or (C1-C6)alkoxy(C1-C6)alkyl group, or a (CH2)nNR7R8, CO2R7, CONHNR7R8, CONR7R8, CONR8OR9, (CH2)nNR7COR8, (CH2)nNR7COOR8 group;

$R_6$ represents a hydrogen atom, a $(C_1-C_4)$alkyl group or one of the values given for $R_5$;

or $R_5$ and $R_6$, as defined above, are bonded together to form a cycle containing 4 to 7 chain links comprising 0 to 2 heteroatoms selected from N and O, said cycle containing 4 to 7 chain links optionally being substituted with one or more substituents independently selected from halogen, $(C_1-C_4)$alkyl, halogenated $(C_1-C_4)$alkyl, hydroxy$(C_1-C_4)$alkyl, $(C_1-C_4)$alkoxy$(C_1-C_4)$alkyl, $(CH_2)_m NR_7R_8$, or a tert-butoxycarbonyl group;

$R_7$ and $R_8$ each independently represent a substituent selected from H, $(C_1-C_4)$alkyl, $(C_1-C_4)$alkyl-OH, $(C_3-C_7)$cycloalkyl, $(C_3-C_7)$cycloalkyl-NH$_2$, $(C_1-C_4)$alkyl-$(C_3-C_7)$cycloalkyl, $C(=NH)NH_2$, $SO_2(C_1-C_6)$alkyl and $SO_2$-phenyl; $R_8$ may also represent a tert-butoxycarbonyl or benzyloxycarbonyl group;

or $R_7$ and $R_8$ together with the nitrogen atom to which they are bonded constitute an azetidinyl, pyrrolidinyl, piperidinyl, piperazinyl or morpholinyl radical, said radical being unsubstituted or substituted one or more times with a $(C_1-C_6)$alkyl, $(C_1-C_4)$alkyl-OH, COO$(C_1-C_6)$alkyl or F group;

$R_9$ represents a hydrogen atom or a (C1-C4)alkyl group;

Ar2 represents a phenyl group which is unsubstituted or substituted 1 to 5 times with similar or different substituents selected from a halogen atom and a (C1-C4)alkyl, trifluoromethyl or (C1-C4)alkoxy group;

n represents 1, 2 or 3;

m represents 0, 1, 2 or 3.

The compounds of formula (I) may comprise one or more asymmetrical carbon atoms. Thus, they may exist in the form of enantiomers or diastereoisomers. Said enantiomers, diastereoisomers and their mixtures including racemic mixtures fall within the scope of the invention. The compounds of formula (I) may exist as bases or as addition salts with acids. When compounds of formula (I) comprise free acid functions, for example carboxylic, sulphonic or phosphonic, said acid functions may be transformed into salts using bases to form addition salts. Said addition salts fall within the scope of the invention.

The addition salts with acids or bases are advantageously prepared with pharmaceutically acceptable acids or bases respectively, but salts of other acids or bases for use, for example, in purifying or isolating compounds of formula (I) also fall within the scope of the invention.

The compounds of formula (I) may also exist in the form of hydrates or solvates, namely in the form of associations or combinations with one or more water molecules or with a solvent. Said hydrates and solvates also fall within the scope of the invention.

The following terms have the following meanings within the context of the invention:

a halogen atom: a fluorine, chlorine, bromine or iodine atom;

an alkyl group: a linear or branched saturated aliphatic group. The following groups may be cited as examples: methyl, ethyl, n-propyl, n-butyl, n-pentyl, n-hexyl, n-heptyl, 1-methylethyl, 1-methylpropyl, 2-methylpropyl, 1,1-dimethylethyl, 1-methylbutyl, 2-methylbutyl, 3-methylbutyl, 1,1-dimethylpropyl, 1,2-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, 1-ethyl-1-methylpropyl, 1-ethyl-2-methylpropyl, 1-ethylbutyl, 2-ethylbutyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 1,1,2,2-tetramethylpropyl, 1-ethylpentyl, 2-ethylpentyl, 3-ethylpentyl, 1-ethyl-1-methylbutyl, 1-ethyl-2-methylbutyl, 1-ethyl-3-methylbutyl, 2-ethyl-1-methylbutyl, 2-ethyl-2-methylbutyl, 2-ethyl-3-methylbutyl, 1-propylbutyl, 1-(1-methylethyl)butyl, 1-(1-methylethyl), 2-methylpropyl;

a cycloalkyl group: cyclopropyl, cyclobutyl, cyclopentyl, cyclohexyl, cycloheptyl, bicyclo[2.2.1]heptyl, cyclooctyl, bicyclo[2.2.2]octyl, bicyclo[3.2.1]octyl, adamantyl.

Preferred compounds of formula (I) in accordance with the invention which may be cited are defined as follows:

$R_1$ represents a tert-butyl, ethyl or phenyl group;

and/or $Ar_1$ represents a radical selected from:

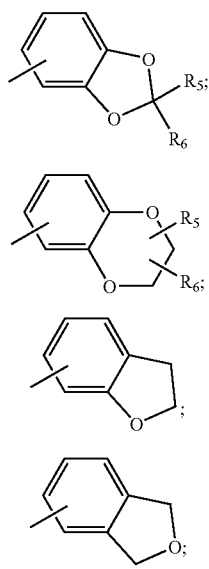

and/or $R_5$ represents a $(CH_2)_nNR_7R_8$, $CONHNR_7R_8$, $CONR_7R_8$, hydroxy$(C_1$-$C_4)$alkyl or $(CH_2)_nNR_7COR_8$ group;

and/or R6 represents a hydrogen atom or a methyl, (CH2)nNR7R8 or hydroxymethyl group;

and/or Ar2 represents an aryl group substituted with 1 or 2 substituents independently selected from a halogen atom or a (C1-C4)alkyl or (C1-C4)alkoxy group;

n, m, $R_7$ and $R_8$ being as defined above for a compound of formula (I);

as a base or as an addition salt with an acid, and also as a hydrate or as a solvate.

The products of the invention will advantageously have a substituent $R_5$ selected from $(CH_2)_nNR_7R_8$, $CONR_7R_8$ and $(CH_2)_nNR_7COR_8$.

A product in accordance with the invention may be present in a non chiral or racemic form or enriched in one stereoisomer or enriched in one enantiomer; it may optionally be in the solvated or hydrated form, and may optionally be in the form of a salt.

In a second aspect, the invention concerns the preparation of synthesis intermediates used in preparing products in accordance with the first aspect of the invention, said intermediates having the following general formula:

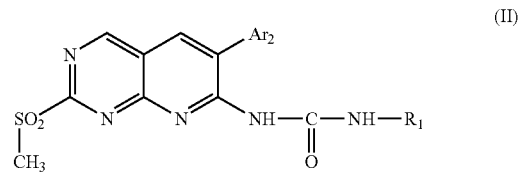

(II)

in which $R_1$ and $Ar_2$ are as defined above.

In a third aspect, the invention concerns the preparation of intermediates in accordance with the first and second aspect of the invention, having the following general formula:

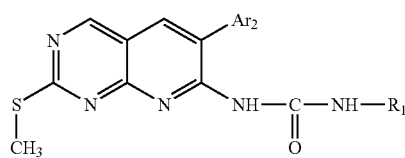

in which R1 and Ar2 are as defined above.

In a fourth aspect, the invention concerns the preparation of intermediates in accordance with the first, second and third aspect, having the following general formula:

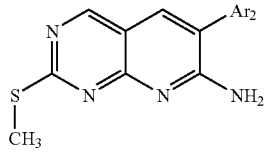

in which $Ar_2$ is as defined above.

Synthesis intermediates in accordance with the second to fourth aspects of the invention comprise a substituent Ar2 selected from phenyl, 2-methoxyphenyl, 2,6-dichlorophenyl, 3,5-dimethoxyphenyl, 3,4-dimethoxyphenyl, 2,6-dibromophenyl, 2-bromo-6-chlorophenyl, 2,4-dichlorophenyl and 3,5-dichlorophenyl.

Synthesis intermediates in accordance with the second and third aspects of the invention comprise a substituent R1 selected from ethyl, tertiobutyl and phenyl.

In accordance with the invention, compounds of formula (I) may be prepared using a process which is characterized in that the following are reacted:
(i) a compound of formula:

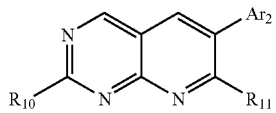

(IIb)

in which $R_{10}$ is a leaving group such as: (a) halogen, in particular Cl or Br or (b) alkyl-S(O)$_m$—, in which m=0, 1, or 2; $R_{11}$ is NHC(=$R_{12}$)—NH—$R_1$, in which $R_{12}$=O or S; and (ii) an amine of formula Ar'$_1$NH$_2$ (III), in which Ar'$_1$ represents Ar$_1$ as defined for (I) or a precursor of Ar$_1$; if appropriate, the group Ar'$_1$ in the compound obtained is transformed into a group Ar$_1$.

When $R_{10}$ is a halogen or alkyl-S(O)$_m$— in which m=2, the reaction is carried out in a solvent, preferably a polar solvent:
(i) for example tetrahydrofuran, dimethylsulphoxide or ethanol, optionally in the presence of a trace of an acid such as hydrochloric acid; or
(ii) in dimethylsulphoxide in the presence of a strong base such as tBuOK;
at a temperature in the range from ambient temperature to the reflux temperature of the solvent.

When $R_{10}$ is alkyl-S(O)m- in which m=0 or 1, the reaction may be carried out with molten Ar'$_1$NH$_2$ (III), preferably at a temperature close to 200° C., with no catalyst.

If appropriate, the amine functions present in the Ar'$_1$ group of compound (III) may have been transformed into salts or may have been protected.

The term "Ar1 precursor" means a group a), b), c), d) or e) as defined above for (I), in which substituents $R_5$ and/or $R_6$ are as defined above for (I) or are precursors of $R_5$ and/or $R_6$.

The compounds of formula (II) are prepared using the operating protocol described in European patent EP-A-0 790 997 and U.S. Pat. No. 5,733,913, as described in Scheme 1 below:

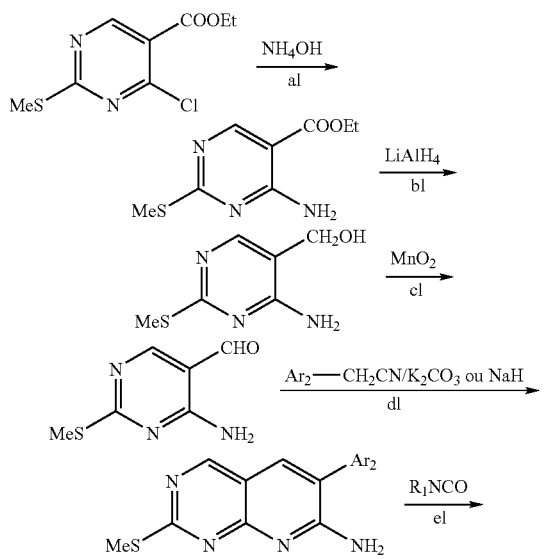

SCHEME 1

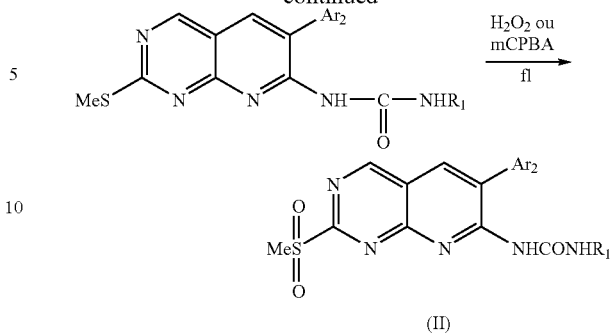

mCPBA: Meta-Chloroperbenzoic Acid.

Amines of formula (III) are known or prepared using known methods from the corresponding nitro compounds Ar'$_1$NO$_2$ (IV), by reduction either (i) in an acid medium in the presence of a metal such as iron or powdered zinc, or (ii) using hydrogen in the presence of a catalyst such as Pd/C.

Compounds of formula (IV) are known or prepared using known methods.

Thus, 5-nitro-1,3-benzodioxoles monosubstituted in the 2-position by a $R_5$=methoxycarbonyl group may be prepared by the action of methyl dichloroacetate on 4-nitro-catechol (4-nitrobenzene-1,2-diol).

5-nitro-1,3-benzodioxoles gem-disubstituted in the 2-position may be prepared in accordance with Pharmazie, 2003, 58 (1), 13-17 by the action of ethyl dibromomalonate on 4-nitrocatechol (4-nitrobenzene-1,2-diol).

7-nitro-2,3-dihydro-1,4-benzodioxines substituted in the 2- or 3-positions with $R_5$ and $R_6$ may be prepared using the method described in International patent WO 01/021 577 from 4-nitrocatechol or using known chemical transformations.

1,3-dihydro-2-benzofuran-5-amine is described in J. Med. Chem., 1978, 21, 965-978; 4H-1,3-benzodioxin-6-amine is described in J. Org. Chem., 1994, 59 (4), 754-757; 4H-1,3-benzodioxin-7-amine is described in Chimie Therapeutique, 1972, 7, 443-449.

Known methods such as those described in March's Advanced Organic Chemistry, 5th Edition, 2005, ISBN 0471585890 can be used to transform the $R_5$ and/or $R_6$ group of compounds of formula (IV), depending on the substituents desired $R_5$ and/or $R_6$ for the compounds of formula (I). Group $R_5$ and/or $R_6$ in compounds of formula (I) may also be transformed to obtain novel compounds of formula (I) carrying the desired substituents $R_5$ and/or $R_6$.

Thus, the group $R_5$=CO$_2$Me can be used to prepare compounds of formula (IV) or (I) in which R5 represents a CO2H, CN, CH2OH, CONR7R8. CONHNR7R8, CONR8OR9 or CH2NR7R8 group using methods which are known in the art.

Starting from a compound of formula (IV) or (I) comprising a group $R_5$=(CH$_2$)$_n$—OH, in which n=1, 2, or 3, a compound of formula (IV) or (I) can be prepared in which $R_5$=mesyloxymethyl by the action of mesyl chloride, followed by a compound of formula (IV) or (I) in which $R_5$=CH$_2$NR$_7$R$_8$ by the action of HNR$_7$R$_8$, R$_7$ and R$_8$ being as defined for compounds of formula (I).

The compounds of the invention are obtained in the racemic form; optically pure isomers may then be prepared using resolution methods which are known to the skilled person, such as crystallization by forming salts with chiral agents. It is also possible to prepare compounds in accordance with the invention in their optically pure form using asymmetric or stereospecific synthesis methods, or chromatographic techniques using a chiral phase. Further, the products of the invention may be separated by forming diastereoisomers, separating them then decomposing the pharmacologically useful diastereoisomer into its enantiomerically pure active product. Enzymatic techniques may also be used. Known supplemental separation techniques may be used. They include those discussed in: Enantiomers, Racemates, and Resolutions, John Wiley and Sons, New York (1981).

The compounds of the invention may also be prepared in a form which is enriched in one stereoisomer while preparing the synthesis intermediates. Hence, the resolution of enantiomers of amines of formula (III) or nitro precursors (IV) may be carried out using known methods.

The following examples describe the preparation of certain intermediates and compounds in accordance with the invention. These examples are not limiting and serve solely to illustrate the present invention.

| MP: | melting point |
|---|---|
| Boc: | tert-butoxycarbonyl |
| BOP: | benzotriazol-1-yloxytris(dimethylamino)phosphonium hexafluorophosphate. |
| THF: | tetrahydrofuran |
| AT: | ambient temperature |
| DCM: | dichloromethane |
| MeOH: | methanol. |
| DCCI: | dicyclohexylcarbodiimide |
| DIPEA: | diisopropylethylamine |
| KHSO4/K2SO4: | 5% solution of KHSO4/K2SO4 |
| Z: | benzyloxycarbonyl |

Proton nuclear magnetic resonance (NMR) spectra were recorded at 200 MHz or at 250 MHz in DMSO-$d_6$, unless otherwise indicated. The DMSO-$d_6$ signal was at 2.5 ppm and acted as a reference. The following abbreviations were used to interpret the spectra: s: singlet, d: doublet, t: triplet, m: broad signal, mt: multiplet, se: broad singlet, dd: double doublet, qd: quadruplet, qt: quintuplet.

Preparation of a Compound of Formula (II)

Preparation 1

N-(t-Butyl)-N'-[6-(2,6-dichlorophenyl)-2-(methylsulphonyl)pyrido[2,3-d]pyrimidin-7-yl]urea 1.1 Ethyl 4-amino-2-(methylthio)pyrimidine-5-carboxylate 140 ml of a 20% NH$_4$OH solution was added to a suspension of 50.7 g of ethyl 4-chloro-2-(methylthio)pyrimidin-5-carboxylate in 400 ml of EtOH over 20 minutes, keeping the temperature at about 20° C. After stirring for 20 hours at ambient temperature, the reaction medium was concentrated under vacuum almost to dryness, then the residue was taken up in 350 ml of water, stirred for 20 minutes, filtered, and washed with 3×60 ml of water then vacuum dried in the presence of P$_2$O$_5$. A white solid was obtained: MP=134-135° C., m=39.9 g.

1.2 [4-Amino-2-(methylthio)pyrimidin-5-yl]methanol 210 ml of a 1M solution of LiAlH$_4$ in THF was added to 39.68 g of the ester obtained in the preceding step dissolved in 1 liter of THF over 45 minutes, keeping the temperature below 30° C. It was stirred for a 1 hour longer, then the temperature was reduced to 5° C. and 9 ml of water, 6.5 ml of 5N sodium hydroxide then 32 ml of water were added, dropwise in succession. After stirring for 10 minutes, the solid was filtered then rinsed with THF. The filtrate was concentrated under vacuum and the residue was re-dissolved in 600 ml of boiling toluene, rapidly hot filtered to eliminate some of the insolubles and the filtrate was allowed to cool overnight. The white crystals obtained were filtered, washed with a little toluene then with ether and dried. MP=124-127° C., m=23.9 g.

1.3 4-Amino-2-(methylthio)pyrimidine-5-carbaldehyde 79.5 g of active MnO2 was added over 2 minutes to a suspension of 23.8 g of alcohol obtained from the preceding step in 1600 ml of chloroform then stirred overnight at ambient temperature; the solid was filtered, washed with 3×75 ml of CHCl3 and the filtrate was concentrated under vacuum to dryness: the white solid residue was taken up in ether, filtered and dried. MP=184-186° C., m=21.05 g.

1.4 6-(2,6-dichlorophenyl)-2-(methylthio)pyrido[2,3-d]pyrimidin-7-amine 5.47 g of 60% NaH was added over 5 minutes to 21 g of the aldehyde obtained in the preceding step dissolved in 240 ml of DMF cooled to 5° C., then 29.05 g of 2,6-dichlorophenylacetonitrile was added over 20 minutes. Stirring was continued for 30 minutes at 5° C. then overnight at ambient temperature. The reaction medium was cooled to 5° C. and 65 ml of a saturated solution of NH$_4$Cl was added followed by 500 ml of a water/ice mixture; a red precipitate was formed which was filtered, washed twice with water, completely drained, washed with ether using 100 ml of chloroform, then again with ether; after drying, a beige solid was obtained. MP=250-253° C., m=29.92 g.

The ether and chloroform wash phases were concentrated to dryness and taken up in a little chloroform to which ether had been added: a second quantity of 3.15 g was obtained. Total m=33.07 g.

1.5 N-(t-Butyl)-N'-[6-(2,6-dichlorophenyl)-2-(methylthio)pyrido[2,3-d]pyrimidin-7-yl]urea 4.6 g of 60% NaH was added over 10 minutes to 29.9 g of the amine obtained above, in solution in 300 ml of DMF, keeping the temperature below 25° C.; it was stirred for a further 20 minutes, then 12.2 ml of tertiobutyl isocyanate was added over 20 minutes followed by stirring overnight. The reaction medium was slowly poured onto 800 ml of a water/ice mixture+100 ml of 6N HCl; the precipitate formed was filtered, washed with water, drained then stirred for 1 hour in 300 ml of ether, followed by filtering, washing with ether and drying. A beige solid was obtained. MP=195-196° C. (dec.), m=26.5 g.

1.6 N-(t-Butyl)-N'-[6-(2,6-dichlorophenyl)-2-(methylsulphonyl)pyrido[2,3-d]pyrimidin-7-yl]urea 27 g of metachloroperbenzoic acid was added to 21.95 g of the urea obtained above, in solution in 300 ml of chloroform, over 25 minutes, keeping the temperature to below 25° C. A precipitate was formed. After 2 hours, the reaction medium was diluted with 1 liter of dichloromethane and Na$_2$SO$_4$ was added, followed by 14 g of Ca(OH)$_2$; after stirring for 30 minutes, the solid was filtered, washed with dichloromethane then the filtrate was concentrated to dryness; the residue was triturated into 80 ml of hot ether; it was allowed to cool then the white solid was filtered, washed with ether and dried. MP=138-140° C., m=20.5 g.

The following compounds of general formula (II) could be prepared in the same manner as that described for the compound described in preparation 1:

metric carbon atom, these compounds were obtained in the racemic form unless otherwise indicated.

Preparation 2

2.1 Methyl 5-nitro-1,3-benzodioxole-2-carboxylate 31.0 g of 4-nitrocatechol was added to 17.6 g of 60% NaH in suspension in 300 ml of DMF over 1 hour, with cooling to

| Ar$_2$ | R$_1$ | NMR |
|---|---|---|
| 2,6-dichlorophenyl | tert-butyl | 1.40: s: 9H; 3.50: s: 3H; 7.50-7.70: m: 3H; 8.55: s: 1H; 9.10: s: 1H; 9.60: s: 1H; 9.95: s: 1H. |
| 2,6-dichlorophenyl | phenyl | 3.50 ppm: s: 3H; 7.10 ppm: t: 1H; 7.40 ppm: t: 2H; 7.55-7.75 ppm: m: 5H; 8.60 ppm: s: 1H; 9.60 ppm: s: 1H; 9.80 ppm: s: 1H; 11.90 ppm: s: 1H. |
| 3,5-dimethoxyphenyl | tert-butyl | 1.40 ppm: s: 9H; 3.50 ppm: s: 3H; 3.80 ppm: s: 6H; 6.65-6.80 ppm: mt: 3H; 7.75 ppm: s: 1H; 8.45 ppm: s: 1H; 9.60 ppm: s: 1H; 9.80 ppm: s: 1H. |
| 2,6-dichlorophenyl | ethyl | 1.20 ppm: t: 3H; 3.40 ppm: qd: 2H; 3.50 ppm: s: 3H; 7.50 ppm-7.75 ppm: m: 3H; 8.55 ppm: s: 1H; 9.40 ppm: s: 1H; 9.60 ppm: s 1H; 9.70 ppm: s: 1H. |
| 3,4-dimethoxyphenyl | tert-butyl | 1.40 ppm: s 9H; 3.45 ppm: s: 3H; 3.80 ppm: s 3H; 3.90 ppm: s: 3H; 7.10-7.20 ppm: m 3H; 7.75 ppm: s: 1H; 8.45 ppm: s 1H; 9.55 ppm: s: 1H; 9.80 ppm: s 1H. |
| phenyl | tert-butyl | 1.40 ppm: s: 9H; 3.50 ppm: s: 3H; 7.60 ppm: se: 6H; 8.45 ppm: s: 1H; 9.40 ppm: s: 1H; 9.80 ppm: s: 1H. |
| 2-methoxyphenyl | tert-butyl | 1.40 ppm: s: 9H; 3, .50 ppm: s: 3H; 3.80 ppm: s: 3H; 7.10-7.40 ppm: mt: 4H; 7.60 ppm: t: 1H; 8.40 ppm: s: 1H; 9.60 ppm: s: 1H; 9.80 ppm: s: 1H. |
| 2,6-dibromophenyl | tert-butyl | 1.40 ppm: s: 9H; 3.50 ppm: s: 3H; 7.40 ppm: t: 1H; 7.85 ppm: d: 2H; 8.50 ppm: s: 1H; 9.00 ppm: s: 1H; 9.60 ppm: s: 1H; 10.00 ppm: s: 1H. |
| 2-bromo-6-chlorophenyl | tert-butyl | 1.40 ppm: s: 9H; 3.45 ppm: s: 3H; 7.50 ppm: t: 1H; 7.65 ppm: d: 1H; 7.80 ppm: d: 1H; 8.50 ppm: s: 1H; 9.00 ppm: s: 1H; 9.50 ppm: s: 1H; 9.90 ppm: s: 1H. |
| 2,6-dibromophenyl | ethyl | 1.15 ppm: t: 3H; 3.30 ppm: qd: 2H (masked by DOH); 3.50 ppm: s: 3H; 7.40 ppm: t: 1H; 7.85 ppm: d: 2H; 8.50 ppm: s: 1H; 9.25 ppm: s: 1H; 9.60 ppm: s: 1H; 9.70 ppm: s: 1H. |
| 2-bromo-6-chlorophenyl | Phenyl | (DMSO + TFA) 3.55 ppm: s: 3H; 7.10 ppm: t: 1H; 7.30-7.90 ppm: m: 7H; 8.60 ppm: s: 1H; 9.65 ppm: s: 1H. |
| 2,6-dibromophenyl | Phenyl | 3.55 ppm: s: 3H; 7.10 ppm: t: 1H; 7.35 ppm: qd: 3H; 7.60 ppm: d: 2H; 7.85 ppm: d: 2H; 8.60 ppm: s: 1H; 9.70 ppm: s: 1H; 9.80 ppm: s: 1H; 12.00 ppm: s: 1H. |
| 2,4-dichlorophenyl | tert-butyl | 1.35 ppm: s: 9H; 3.50 ppm: s: 3H; 7.45-7.60 ppm: mt: 2H; 7.80 ppm: s: 1H; 8.40 ppm: s: 1H; 8.80 ppm: s: 1H; 9.55 ppm: s: 1H; 9.80 ppm: s: 1H. |

Preparation of Compounds of Formula (III)

The preparation numbers relate to the numbers of the compounds in Tables 1 and 2 below. When they contain an asymkeep the temperature below 30° C. Stirring was continued for 15 minutes then 104 ml of methyl dichloroacetate was added over 1 hour, and stirring was continued for 4 hours at 90° C. The reaction medium was poured over a mixture of 2 liters of ice/water then extracted 4 times with 400 ml of AcOEt. The combined organic phases were washed once with a saturated NaCl solution then dried and concentrated under vacuum (DMF evaporated off). The residue was taken up in a AcOEt/H$_2$0 mixture and the pH was brought to 8.6 using Na$_2$CO$_3$; the organic phase was decanted, washed with saturated NaHCO$_3$, H$_2$O, 5% KHSO$_4$/K$_2$SO$_4$, H$_2$O, saturated NaCl then dried and vacuum evaporated; a semi-solid residue was obtained which was taken up then triturated in heptane to produce a solid.

m=27.7 g, MP=90-92° C.

2.2 Methyl 5-amino-1,3-benzodioxole-2-carboxylate 3.92 g of powdered zinc was added to 900 mg of the ester from the preceding step, dissolved in 30 ml of THF and, after cooling to −5° C., 4 ml of acetic acid diluted with 4 ml of THF was added over 30 minutes, then the temperature was allowed to rise. After 1½ hours, filtration was carried out and the solid was washed with a little THF and methanol. The filtrate was diluted with AcOEt and washed with H$_2$O, saturated NaHCO$_3$, H$_2$O, saturated NaCl; after drying and concentration under vacuum, a yellow wax was obtained which was identified by NMR. m=800 mg.

Preparation 3

3.1 5-Nitro-1,3-benzodioxole-2-carboxamide 20 ml of a 2M ammoniacal solution in methanol was poured onto 1.12 g of the methyl ester from preparation 2.1. After 25 minutes, it was concentrated under vacuum, the solid residue was taken up in Et2O, filtered and dried. m=0.99 g; MP=202-207° C.

3.2 5-Amino-1,3-benzodioxole-2-carboxamide 4.57 g of powdered zinc was added to 0.98 g of the amide from preparation 3.1 in 35 ml of THF; after cooling to −5° C., 5 ml of acetic acid diluted in 5 ml of THF was added over 30 minutes. Following addition, the temperature was allowed to rise. After 1 hour, the solid was filtered, washed with a little THF, methanol, AcOEt. The filtrate was diluted with AcOEt, water was added thereto and the pH was brought to 6 with saturated NaHCO3. The precipitate formed was eliminated by filtering, the filtrate was decanted and then the organic phase was washed with saturated NaHCO3, H2O, saturated NaCl, then dried and evaporated; a wax which hardened on cooling was obtained. m=0.63 g.

Preparation 4

4.1 5-Nitro-(1,3-benzodioxol-2-yl)methanol 22.3 ml of a 1M solution of LiAlH4 in THF was added to 5.02 g of the methyl ester obtained in preparation 2.1, dissolved in 25 ml of THF, at −5° C. over 1 hour 15 minutes; 20 minutes after addition was complete, 20 ml of AcOEt then 9 ml of 1N NaOH was added dropwise; the precipitate formed was eliminated by filtration, washed with AcOEt; the filtrate was diluted with AcOEt and washed with H2O, 5% KHSO4/K2SO4, H2O, saturated NaCl; after drying and concentration under vacuum, a wax was obtained which crystallized. m=2.74 g, MP=80-82° C.

In the next step, the nitro derivative from preparation 4.1 was reduced using the methods described above to produce the amine of formula (III) described in Preparation 4.2.

Preparation 5

5.1 (5-Nitro-1,3-benzodioxol-2-yl)methylsulphonate 3 ml of triethylamine was added at 5° C. to 4.12 g of the alcohol obtained in preparation 4.1 dissolved in 30 ml of CH2Cl2, followed by 1.85 g of mesyl chloride over 15 minutes. After 15 minutes, the ice bath was removed. After 55 minutes, the reaction medium was diluted with CH2Cl2 and water; the organic phase was decanted, washed with H2O, saturated NaCl, dried, evaporated. After trituration in heptane, a brown solid was obtained. m=5.20 g, MP=112-115° C.

5.2 [(5-Nitro-1,3-benzodioxol-2-yl)methyl]diethylamine 2.19 g of diethylamine was added to 2.91 g of the mesylate obtained in the preceding step in 18 ml of DMF, then heated to 80° C. 0.73 g of diethylamine was added after 15 hours followed by a further 0.73 g after 8 hours.

After a total of 48 hours, the reaction medium was diluted with AcOEt, washed with H2O then with saturated NaCl; after drying, the AcOEt had evaporated off and the residue was taken up in 40 ml of Et2O+10 ml of AcOEt and extracted twice with 60 ml of 0.25N HCl; the acid phases were mixed, brought into contact with AcOEt and the pH was brought to 9 with 10N NaOH; the organic phase was decanted off, washed with H2O then with saturated NaCl, then dried and evaporated. An oil was obtained. m=1.55 g.

5.3 [(5-Amino-1,3-benzodioxol-2-yl)methyl]diethylamine 7.45 g of powdered zinc was added to 1.93 g of the nitro compound obtained in the preceding step, dissolved in 70 ml of THF, then at −5° C., 7.6 ml of AcOH was added over 25 minutes and stirring was continued between 0° C. and 5° C.

After 1½ hours, the solid was filtered, washed with THF and a little methanol; the filtrate was diluted with AcOEt+H2O and the pH was brought to 9 with 10N NaOH; the precipitate formed was eliminated by filtering; the filtrate was decanted; the organic phase was washed with H2O, saturated NaCl, dried and evaporated off to obtain a black oil. m=1.75 g.

Preparation 6

6.1 1-Methyl-4-((5-nitro-1,3-benzodioxol-2-yl)methyl)piperazine

The reaction followed operating protocol 5.2; the product was isolated in the form of the dihydrochloride.

6.2 2-((Methylpiperazin-1-yl)methyl)-1,3-benzodioxol-5-amine

The reaction followed operating protocol 5.3.

Preparation 7

7.1 5-nitro-1,3-benzodioxol-2-carboxylic acid 1.5 ml of 5N NaOH was added over 30 minutes to 1.12 g of the ester obtained in preparation 2.1 in 12 ml of methanol. 35 minutes after addition was complete, the reaction medium was diluted with AcOEt and H2O and the pH was brought to 2 with 2N HCl; the organic phase was decanted, washed with H2O and saturated NaCl, then dried and evaporated to obtain 1.25 g of oil.

7.2 N,N-Dimethyl-5-nitro-1,3-benzodioxol-2-carboxamide 0.36 g of dimethylamine hydrochloride, 0.77 ml of DIPEA then 0.91 g of DCCI were added to 0.84 g of the acid obtained in the preceding step dissolved in 15 ml of dichloromethane. After stirring for 3 hours at ambient temperature, the reaction medium was filtered and the filtrate was diluted with CH2Cl2 and washed in succession with a solution of saturated NaHCO3, H2O, 5% KHSO4/K2SO4, H2O, saturated NaCl; after drying, the solvent was evaporated off then the residue was chromatographed on silica using a 99/1 dichloromethane/methanol mixture. 0.5 g of solid product was obtained. MP=109° C.

Preparation 9

9.1 5-Nitro-1,3-benzodioxol-2-carbonitrile 3.7 ml of POCl3 was added to 45 ml of DMF cooled to 5° C. After stirring for 30 minutes at 5° C., 1.67 g of the amide obtained in preparation 3.1 was added all at once. After stirring for 3 hours at ambient temperature, the reaction mixture was poured onto a mixture of 250 ml of water/ice. The precipitate formed was filtered, washed with water then dried. m=1.32 g; MP=105-110° C.

9.2 5-Amino-1,3-benzodioxol-2-carbonitrile

Reduction of the nitro group of the product obtained in step 9.1 using NH2 was carried out employing the method described above, using a Zn/AcOH mixture.

Preparation 11

11.1 Ethyl 5-nitro-1,3-benzodioxol-2,2-dicarboxylate

This compound was prepared using the operating protocol described in Pharmazie 2003 58 (1) 13-17.

11.2 5-Nitro-1,3-benzodioxol-2,2-dicarboxamide 1.24 g of the diester obtained in the preceding step was added all at once to 14 ml of a 2M ammoniacal solution in methanol. After stirring for 30 minutes, the reaction medium was concentrated to dryness then the solid residue was taken up in ether, filtered and dried. m=1.01 g; MP=231-233° C.

Preparation 12

12.1 (5-Nitro-1,3-benzodioxol-2,2-diyl)dimethanol 1.50 g of NaBH4 was added to 1.87 g of the diester obtained in preparation 11.1 in 60 ml of THF, at ambient temperature and over 1 hour; 25 minutes after addition was complete, it was diluted dropwise with 250 ml of AcOEt then 5 ml of methanol then 40 ml of water. The organic phase was decanted, washed with H2O, 5% KHSO4/K2SO4 solution, H2O, then saturated NaCl solution. After evaporating to dryness, the residue was chromatographed on silica with a chloroform/methanol mixture (98/2) and 0.64 g of an oil was obtained which set. MP=111-113° C.

Preparation 13

13.1 Ethyl 3-(2-methyl-5-nitro-1,3-benzodioxol-2-yl)propanoate 22.4 g of phosphoric anhydride was added to 15.51 g of 4-nitrocatechol in suspension in 22.10 g of ethyl acetoacetate at 70° C. over 15 minutes. After 1 hour 45 minutes, the reaction medium was cooled then extracted with 4×150 ml of tepid toluene. The toluene phases were combined, washed with H2O, 1N NaOH, H2O, 5% KHSO4/K2SO4, H2O and a saturated NaCl solution. After drying and evaporating, the product was purified by silica chromatography, eluting with chloroform, to obtain 2.44 g of solid. MP=76-78° C.

13.2 3-(2-methyl-5-nitro-1,3-benzodioxol-2-yl)propan-1-ol 8 ml of 1M LiAlH4 in THF was added to 2.33 g of the ester obtained above, dissolved in 40 ml of THF, at −5° C. over 45 minutes. After 35 minutes, 8 ml of ethyl acetate was added dropwise, followed by 1 ml of water then 1 ml of 1N NaOH. The solid was eliminated by filtration; the filtrate was diluted with AcOEt, washed with H2O, 5% KHSO4/K2SO4, saturated NaCl; after drying, the organic phase was concentrated under vacuum; an oil was obtained. m=1.90 g.

13.3 3-(2-methyl-5-nitro-1,3-benzodioxol-2-yl)propylmethanesulphonate 1.01 g of triethylamine then 1.14 g of mesyl chloride were added to 1.89 g of the alcohol obtained in the preceding step 13.2, in 40 ml of dichloromethane at 5° C., over 20 minutes. Following addition, the ice bath was removed and stirring was continued for 1 hour; the reaction medium was diluted with CH2Cl2 and washed with H2O, then with a saturated NaCl solution; after drying, the solvent was evaporated off; 2.46 g of wax was obtained which solidified when cold.

13.4 N,N-diethyl-3-(2-methyl-5-nitro-1,3-benzodioxol-2-yl)propan-1-amine 0.87 g of diethylamine was added to 1.21 g of mesylate in 20 ml of DMF then heated to 80° C. After 81-2 hours, 0.44 g of diethylamine was added and heating was continued for 14 hours. The reaction medium was concentrated under vacuum, the residue was re-dissolved in AcOEt and the pH was brought to 9.5 with 1N NaOH; the organic phase was decanted, washed with H2O, a saturated NaCl solution, then dried; after evaporation, the crude product was obtained which was re-dissolved in 20 ml of AcOEt plus 20 ml of Et2O and extracted twice with 50 ml of 0.5N HCl; the two aqueous phases were mixed, brought into contact with AcOEt and the pH was brought to 9 using 10N NaOH; the organic phase was decanted, washed again with H2O then with a saturated NaCl solution, dried, evaporated, and 0.66 g of oil was obtained.

13.5

The NO2 substituent of the product obtained in step 13.4 was reduced to NH2 using the method described above using a Zn/AcOH mixture, to obtain a reduced product 13.5.

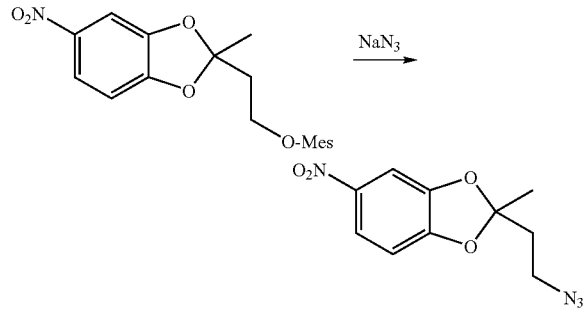

0.85 g of sodium nitride was added to 2.00 g of the product obtained in preparation 13.3 in 20 ml of DMF and stirred for 5 days at ambient temperature, extracted with ether and the organic phase was washed with water then with a saturated NaCl solution. An oil was obtained. m=1.50 g. NMR in agreement.

13.7

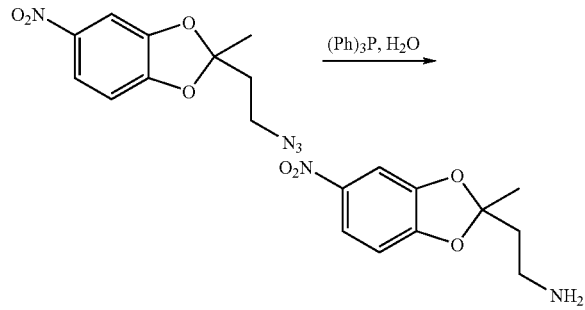

A mixture of 1.49 g of the product obtained in preparation 13.6, 1.71 g of triphenylphosphine and 0.12 g of water in 25 ml of THF was stirred for 24 hours. The reaction medium was then extracted with AcOEt and washed with water. The crude product obtained was dissolved in a AcOEt/Et$_2$O mixture and extracted with an aqueous solution of 1N HCl. The aqueous acid phase was brought into contact with AcOEt and the pH was brought to 9 with 10N NaOH. The organic phase was isolated, washed with water, then with a saturated NaCl solution. The organic phase was concentrated under reduced pressure to obtain 1.10 g of oil.

13.8

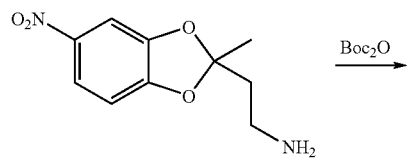

-continued

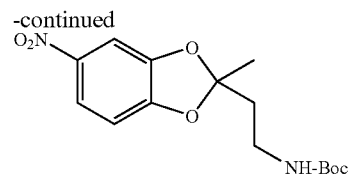

1.09 g of the amine obtained in step 13.7 was dissolved in 10 ml of dichloromethane (DCM) then 0.20 g of triethylamine and 1.18 g of Boc$_2$O were added. After 5 hours, the reaction medium was diluted with DCM then washed in succession with a 5% KHSO$_4$/K$_2$SO$_4$ solution, water, and a saturated NaCl solution. After drying and evaporating the isolated organic phase under reduced pressure, 1.36 g of oil was obtained.

13.9 (Precursor for Example 55)

1.35 g of the product obtained in step 13.8 was treated with Zn/AcOH as described in preparation 2.2 to reduce the NO$_2$ group to NH$_2$. 1.13 g of wax was obtained.

Preparation 14

14.1 2-(2-Methoxymethyl)-5-nitro-1,3-benzodioxole 1.45 g of hydroxymethyl obtained in preparation 4.1 was dissolved in 25 ml of THF; after cooling to 5° C., 353 mg of 60% NaH was added in small fractions; after 30 minutes, 0.92 ml of methyl iodide was added followed by stirring overnight at ambient temperature; 1 ml of methyl iodide was added and stirring was continued for 5 hours; 30 ml of saturated NH$_4$Cl solution was added to the reaction medium followed by water and ethyl acetate; the organic phase was decanted, washed again with H$_2$O then with saturated NaCl, dried and evaporated. The crude product was chromatographed on silica, eluting with 9/1 CHCl$_3$/heptane. 595 mg of oil was obtained and identified using NMR.

Preparation 16

16.1 Tert-butyl 2-((5-nitro-1,3-benzodioxol-2-yl)carbonyl)hydrazinecarboxylate

A mixture of 900 mg of the ester (preparation 2.1) and 2.114 g of tertiobutylcarbazate in 40 ml of methanol was heated at 60° C. for 60 hours; 600 mg of tertiobutylcarbazate was added and heating was continued for 3 hours. The methanol was evaporated off, the residue was taken up in ethyl acetate and washed with water, 0.2N hydrochloric acid, a saturated sodium bicarbonate solution, water and a saturated NaCl solution. A wax was obtained which set. m=1.27 g.

16.2 Tert-butyl 2-((5-amino-1,3-benzodioxol-2-yl)carbonyl)hydrazinecarboxylate 3.92 g of powdered zinc was added to 1.30 g of the product obtained in the preceding step dissolved in 25 ml of THF then, at −5° C., 4.8 g of acetic acid was added over 30 minutes; the ice bath was removed and stirring was continued for 2 hours; the solid was filtered, washed with a little THF then with AcOEt; water was added to the filtrate and the pH was brought to 6.5 with a 15% Na2CO3 solution; the AcOEt was decanted, washed with saturated NaHCO3, H2O, saturated NaCl, dried and evaporated. The expected compound was obtained in the form of a black oil.

m=1.12 g.

Preparation 21

21.1

1.51 g of sodium azide was added to 2.14 g of the mesylate obtained in step 5.1 dissolved in 17 ml of DMF, and heated to 70° C. for 3 hours. The reaction mixture was extracted with AcOEt then washed with water then with a saturated NaCl solution. An oil was obtained. m=1.71 g.

21.2

3.41 g of triphenylphosphine was added in small portions to 1.7 g of the product obtained in step 21.1 dissolved in 20 ml of AcOEt, then after 10 minutes, 2.34 ml of water was added and heated to 60° C. After 1 hour, the reaction mixture was evaporated to dryness, and taken up in Et2O. The insolubles were eliminated then an excess of a solution of saturated HCl in ether was added. The solid formed was filtered, washed with ether then dried to obtain the expected product in the form of the hydrochloride. The corresponding amine was obtained by liberating the hydrochloride.

21.3

The product obtained in step 21.2 could be separated into its two enantiomers:

1.97 g of (S)(+)mandelic acid was added to 2 g of the amine obtained in step 21.2 dissolved in 70 ml of water and 7 ml of dioxane at 70° C. The reaction medium was then allowed to return slowly to 30° C. with magnetic stirring. The precipitate obtained was filtered, dissolved in 40 ml of water and 4 ml of dioxane at 70° C., then was allowed to return slowly to 30° C. with stirring. The solid which formed during cooling was filtered and dried. m=0.49 g.

The product obtained was taken up in 20 ml of water and 100 ml of AcOEt then was brought to a pH of 9.5 by adding 1N NaOH. The mixture was decanted, the organic phase was isolated, washed several times with water then with a saturated NaHCO$_3$ solution, with water, and finally with a saturated NaCl solution. The organic phase was collected, dried and the solvent was evaporated off under reduced pressure. 0.27 g of a wax was obtained which slowly hardened. [α]D=+94.7°, at 25° C.; C=0.5 (MeOH); optical purity: chiral HPLC: 96/4 (rotatory power of 100% purified enantiomer=102°).

21.4

1.49 ml of triethylamine was added to the product obtained in step 21.2 in 30 ml of DCM, then 2.53 g of Boc2O was added in small portions. After 1 hour, the reaction medium was washed with 5% KHSO4/K2SO4, H2O, saturated NaCl.

After drying, the organic phase was concentrated to dryness then the residue was triturated in heptane; 2 g of solid was obtained.

21.5

1.79 g of the product obtained in step 21.4 dissolved in 15 ml of THF was added to 480 mg of NaH in 20 ml of THF at 5° C. over 30 minutes. The mixture was stirred for 45 minutes at ambient temperature then 1.2 ml of iodomethane was added over 10 minutes. After 3 hours, the reaction medium was poured onto 60 ml of a saturated aqueous solution of citric acid then extracted with ethyl acetate. The organic phase was isolated, washed with water then with a saturated NaCl solution, dried and evaporated to dryness. The crude product obtained was purified by flash chromatography with a dichloromethane gradient in cyclohexane. A white solid was obtained. m=1.4 g.

21.6

The product from preparation 21.5 was reduced using the usual method employing Zn/AcOH.

Preparation 22

22.1

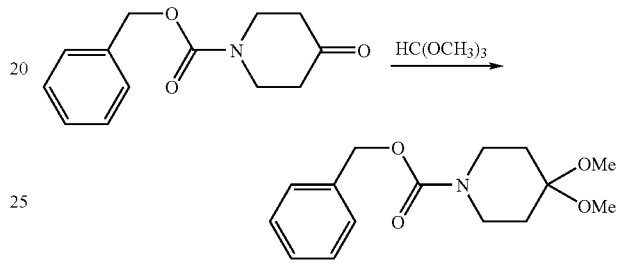

A mixture of 11.65 g of 4-N-Z-piperidone, 6.35 g of methyl orthoformate and 40 mg of para-toluenesulphonic acid was heated in a Claisen reactor at 60° C. for 1 hour then at 70° C. for 1 hour, allowing the methyl formate to distill. The residue was diluted with AcOEt+H2O and several drops of 1N sodium hydroxide were added to bring the pH to 7. The organic phase was decanted, isolated, washed with water then with a saturated NaCl solution, dried and evaporated off. 14 g of colourless oil was obtained.

22.2

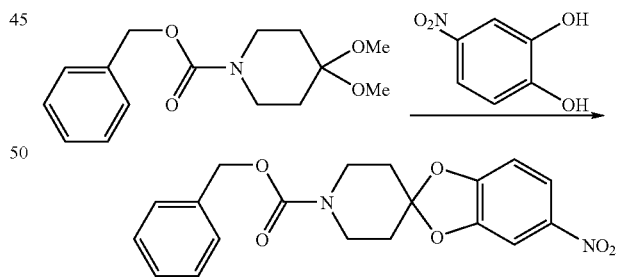

16.09 g of the ketal obtained in step 22.1, 10.80 g of 4-nitrocatechol and 60 mg of para-toluenesulphonic acid were heated in 120 ml of toluene with slow distillation of the toluene. After 4 h30, the reaction medium was diluted with toluene and cooled, the insolubles were eliminated by filtration, the filtrate was washed with 1N NaOH, H2O, a 5% KHSO4/K2SO4 solution, H2O and saturated NaCl. After drying and evaporating off, the crude product was chromatographed on silica, eluting with 98/2 CHCl3/AcOEt. 0.65 g of the expected product was obtained.

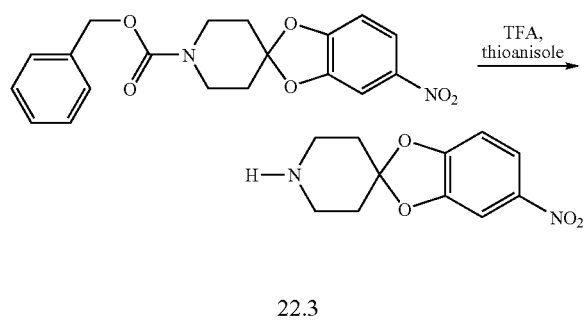

22.3

0.5 ml of thioanisole was added to 0.60 g of the product obtained above in 5 ml of trifluoroacetic acid. After 3 h, the reaction medium was concentrated under vacuum; the residue was taken up in CH2Cl2 with H2O and brought to a pH of 9 with 1N NaOH. After decanting, the organic phase was washed again with water then with a saturated NaCl solution. The organic phase was dried and evaporated. The recovered crude product was chromatographed on silica with 95/5/0.1 CHCl3/MeOH/NH4OH. 100 mg of the expected product was obtained as a solid.

22.4

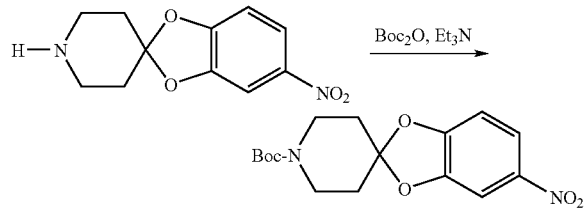

95 mg of the amine obtained in step 22.3 was treated with 98 mg of Boc2O and 20 mg of triethylamine in 3.5 ml of dichloromethane for 1 h. After the usual reaction and treatment, a white solid was obtained. m=130 mg.

22.5

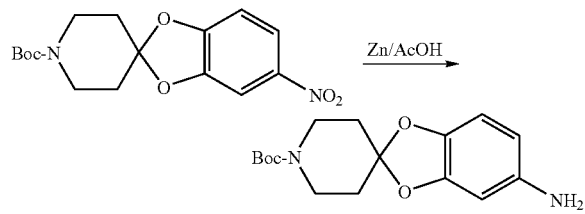

The NO2 group was reduced to amine using Zn/AcOH employing the operating protocol described above.

23.1

0.46 ml of pyridine was added to 985 mg of the product produced in preparation 4.1 dissolved in 25 ml of DCM. 0.84 ml of triflic anhydride dissolved in 3 ml of DCM was then added over 20 minutes at 5° C. After 1 h at 5° C., the reaction medium was washed with ice water then with a saturated NaCl solution. The organic phase was dried and concentrated under vacuum. 1.42 g of solid was obtained.

23.2

75 mg of diethanolamine was added to 1.15 g of the product obtained in step 23.1 dissolved in 10 ml of DCM+0.5 ml of DMF. After stirring overnight, the reaction medium was diluted with 100 ml of DCM, washed with water, washed with a saturated NaCl solution, dried and concentrated under reduced pressure. The residue was purified by flash chromatography using a methanol gradient of 0 to 15% in chloroform. 730 mg of solid was obtained.

23.3

The NO2 group was reduced to the amine by Zn/AcOH as described above. Starting from 720 mg of the product obtained in step 23.2, 400 mg of the expected product was obtained in the form of a gum.

Preparation 24

24.1

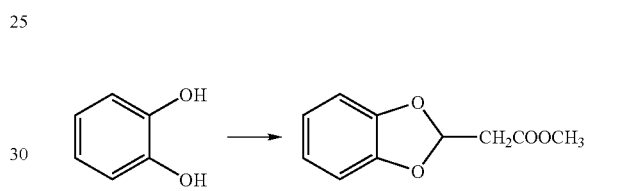

The product was prepared using the operating protocol described in Org. Lett. 2001, 3(9), 1399-1402.

Preparation 24.2

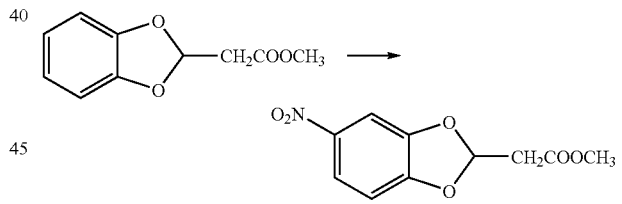

Racemic 5 ml of 69% nitric acid was added over 2 minutes to 2.73 g of the product obtained in 24.1 in 30 ml of DCM. After stirring for 2 h 30 mins, the reaction medium was diluted with Et2O; the organic phase was washed twice with H2O, twice with a 7% iced Na2CO3 solution, once with water, once with a 5% KHSO4/K2SO4 solution, once with water then once with a saturated NaCl solution. After drying and evaporating, a white solid was obtained. m=3.20 g.

Preparation 24.3

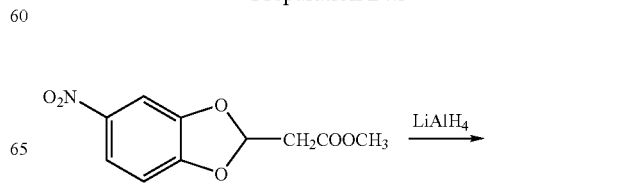

-continued

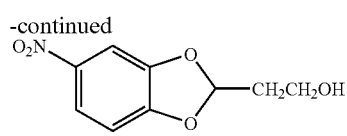

3.63 g of the product obtained using the operating protocol described above in 80 ml of THF was treated with 532 mg of LiAlH4 at −5° C. for 1 h. After the usual treatment, 2.60 g of product was isolated in the form of a thick oil.

Preparation 24.4

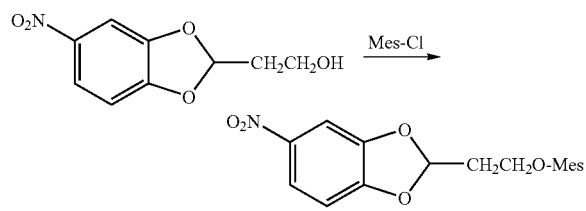

2.59 g of the alcohol obtained in step 24.3 was treated with mesyl chloride as described in the operating protocol described in preparation 13.3 to give 3.52 g of mesylate. It was identified by NMR.

Preparation 24.5

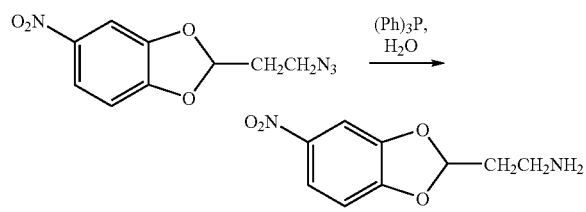

3.51 g of the product obtained in step 24.4 was treated with 1.97 g of sodium azide using the operating protocol described in preparation 13.6. 2.60 g of the expected product was obtained.

Preparation 24.6

2.59 g of the product obtained in step 24.5 was treated with 4.90 g of triphenylphosphine and 2 ml of water using the operating protocol described in preparation 13.7. 2 g of the expected product was obtained as an oil.

Preparation 24.7

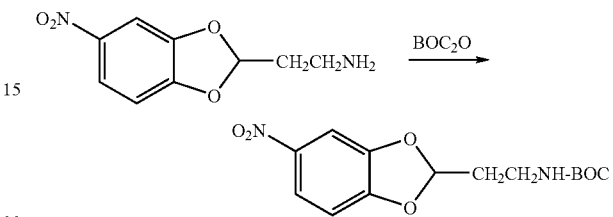

1.99 g of the product obtained in step 24.6 was treated with $BOC_2O$ using the operating protocol described in preparation 13.8. 2.41 g of solid was obtained.

Preparation 24.8

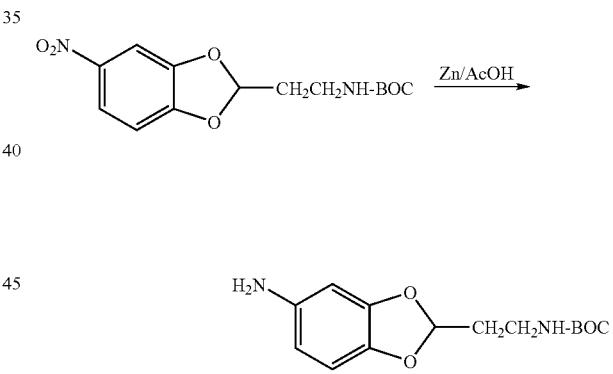

The product obtained in step 24.7 was treated with Zn/AcOH using the usual protocol to reduce the nitro group to an amino group. 0.84 g of the expected product, in the form of a wax, was obtained from 0.93 g of starting product.

The compounds of formula (III) and intermediates of formula (IV), all benzodioxole derivatives, are characterized in the table below.

Transformation of the compound of formula (IV) into a compound of formula (III) was carried out using preparation 5.3 for the following compounds: 7.2, 9.1, 11.1, 12.1, 13.4 and 14.1.

TABLE 1

Preparations of compounds of formula (III).

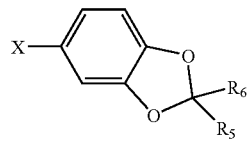

| Preparations | CR$_5$R$_6$ | X = NO$_2$ (IV) NMR | X = NH$_2$ (III) NMR |
|---|---|---|---|
| 2 | CH—CO$_2$Me | 2.1<br>3.80 ppm: s: 3 H;<br>6.95 ppm: s: 1 H;<br>7.25 ppm: d: 1 H<br>7.85-8.00 ppm: m: 2 H | 2.2<br>3.80 ppm: s: 3 H;<br>4.90 ppm: se: 2 H;<br>6.10 ppm: dd: 1 H;<br>6.35 ppm: d: 1 H;<br>6.55 ppm: s: 1 H;<br>6.75 ppm: d: 1 H |
| 3 | CH—CONH$_2$ | 3.1<br>6.60 ppm: s: 1 H;<br>7.25 ppm: d: 1 H;<br>7.80-8.30 ppm: m: 4 H | 3.2<br>4.80 ppm: se: 2 H;<br>6.00 ppm: dd: 1 H;<br>6.10 ppm: s: 1 H;<br>6.25 ppm: d: 1 H;<br>6.60 ppm: d: 1 H;<br>7.65 ppm: se: 1 H;<br>7.90 ppm: se: 1 H |
| 4 | CH—CH$_2$OH | 4.1<br>3.75 ppm: m: 2 H;<br>5.40 ppm: t: 1 H;<br>6.55 ppm: t: 1 H;<br>7.10 ppm: d: 1 H;<br>7.75 ppm: d: 1 H;<br>7.90 ppm: dd: 1 H | 4.2<br>3.65 ppm: m: 2 H;<br>4.70 ppm: se: 2 H;<br>5.25 ppm: t: 1 H;<br>5.90-6.05 ppm: m: 2 H;<br>6.20 ppm: d: 1 H;<br>6.55 ppm: t: 1 H |
| 5 | CH—CH$_2$NEt$_2$ | 5.2<br>0.95 ppm: t: 6 H;<br>2.55 ppm: qd: 4 H;<br>2.95 ppm: d: 2 H;<br>6.55 ppm: t: 1 H;<br>7.10 ppm: d: 1 H;<br>7.70 ppm: d: 1 H;<br>7.90 ppm: dd: 1 H | 5.3<br>0.85 ppm: t: 6 H;<br>2.45 ppm: qd: 4 H;<br>2.65 ppm: d: 2 H;<br>4.55 ppm: se: 2 H;<br>5.75-5.90 ppm: m: 2 H;<br>6.05 ppm: d: 1 H;<br>6.40: d: 1 H |
| 6 | CH—CH$_2$—N(piperazine)N-Me | 6.1<br>2.60 ppm: s: 3 H;<br>2.70-3.40 ppm: m: 10 H;<br>6.65 ppm: t: 1 H;<br>7.05 ppm: d: 1 H;<br>7.65 ppm: d: 1 H;<br>7.80 ppm: dd: 1 H | 6.2<br>2.30-2.70 ppm: m: 11 H;<br>2.80 ppm: d: 2 H;<br>4.80 ppm: se: 2 H;<br>6.00 ppm: dd: 1 H;<br>6.15 ppm: t: 1 H;<br>6.20 ppm: d: 1 H;<br>6.60 ppm: d: 1 H |
| 7 | CH—CONHMe$_2$ | 7.2<br>2.85 ppm: s: 3 H;<br>3.10 ppm: s: 3 H;<br>7.15 ppm: d: 1 H;<br>7.35 ppm: s: 1 H;<br>7.80 ppm: d: 1 H;<br>7.90 ppm: dd: 1 H | 7.3<br>2.85 ppm: s: 3 H;<br>3.05 ppm: s: 3 H;<br>4.80 ppm: se: 2 H;<br>6.00 ppm: dd: 1 H;<br>6.20 ppm: d: 1 H;<br>6.60 ppm: d: 1 H;<br>6.75 ppm: s: 1 H |
| 8 | CH—CONHEt | 8.1<br>1.00 ppm: s: 3 H;<br>3.10 ppm: qt: 2 H;<br>6.50 ppm: s: 1 H;<br>7.10 ppm: d: 1 H;<br>7.70 ppm: d: 1 H;<br>7.85 ppm: dd: 1 H;<br>8.70 ppm: te: 1 H | 8.2<br>1.00 ppm: t: 3 H;<br>3.05 ppm: qt: 2 H;<br>4.70 ppm: se: 2 H;<br>5.95 ppm: dd: 1 H;<br>6.05 ppm: s: 1 H;<br>6.15 ppm: d: 1 H;<br>6.50 ppm: d: 1 H;<br>8.40 ppm: te: 1 H |
| 9 | CH—CN | 9.1<br>7.30 ppm: d: 1 H;<br>7.45 ppm: s: 1 H;<br>8.05-8.85 ppm: m: 2 H | 9.2<br>5.10 ppm: se: 2 H;<br>6.20 ppm: dd: 1 H;<br>6.45 ppm: d: 1 H;<br>6.85 ppm d: 1 H;<br>7.25 ppm: s: 1 H |
| 10 | CH—CONHMe$_2$ | 10.1<br>2.50 ppm: s: 6 H;<br>6.50 ppm: s: 1 H; | 10.2<br>2.50 ppm: s: 6 H;<br>4.75 ppm: se: 2 H; |

TABLE 1-continued

Preparations of compounds of formula (III).

[Structure: benzodioxole with X substituent on benzene ring and R5, R6 on dioxole carbon]

| Prepara-tions | CR5R6 | X = NO2 (IV) NMR | X = NH2 (III) NMR |
|---|---|---|---|
| | | 7.10-7.20 ppm: m: 1H; 7.75-7.80 ppm: m: 1 H; 7.85-7.95 ppm: m: 1 H; 9.80 ppm: se: 1 H | 5.95-6.50 ppm: m: 4 H; 9.50 ppm: se: 1 H |
| 11 | C(CONH2)(CONH2) | 11.1 7.05 ppm: 1 H; 7.65 ppm: d: 1 H; 7.80 ppm: dd: 1 H; 7.90 ppm: se: 2 H; 8.05 ppm: se: 2 H | 11.2 4.80 ppm: se: 2 H; 6.00 ppm: dd: 1 H; 6.20 ppm: d: 1 H; 6.55 ppm: d: 1 H; 7.70 ppm: de: 4 H |
| 12 | C(CH2OH)(CH2OH) | 12.1 3.80 ppm: d: 4 H; 5.40 ppm: t: 2 H; 7.05 ppm: d: 1 H; 7.65 ppm: d: 1 H; 7.85 ppm: dd: 1 H | 12.2 3.45 ppm: d: 4 H; 4.50 ppm: se: 2 H; 5.05 ppm: t: 2 H; 5.80 ppm: dd: 1 H; 6.05 ppm: d: 1 H; 6.35 ppm: d: 1 H |
| 13 | C(CH2CH2—NEt2)(Me) | 13.4 0.90 ppm: t: 6 H; 1.70 ppm: s: 3 H; 2.10-2.60 ppm: m: 8 H; 7.05 ppm: d: 1 H; 7.70 ppm: d: 1 H; 7.85 ppm: dd: 1 H. | 13.5 0.90 ppm: t: 6 H; 1.50 ppm: s: 3 H; 1.85-2.00 ppm: m: 2 H; 2.30-2.60 ppm: m: 6 H; 4.60 ppm: se: 2 H; 5.90 ppm: dd: 1 H; 6.10 ppm: d: 1 H; 6.45 ppm: d: 1 H |
| 13a | C(CH2CH2—NH-Boc)(Me) | 13.8 1.35 ppm: s: 9 H; 1.45 ppm: s: 3 H; 2.10-2.20 ppm: m: 2 H; 3.0-3.10 ppm: m: 2 H; 6.80-6.90 ppm: m: 1 H; 7.01 ppm: d: 1 H; 7.65 ppm: d: 1 H; 7.85 ppm: dd: 1 H. | 13.9 1.35 ppm: s: 9 H; 1.45 ppm: s: 3 H; 1.90-2.05 ppm: m: 2 H; 2.95-3.10 ppm: m: 2 H; 4.60 ppm: se: 2 H; 5.95 ppm: dd: 1 H; 6.15 ppm: d: 1 H; 6.45 ppm: d: 1 H; 6.75 ppm: t: 1 H. |
| 14 | CH—CH2OMe | 14.1 3.30 ppm: s: 3 H; 3.75 ppm: d: 2 H; 6.60 ppm: t: 1 H; 7.10 ppm: d: 1 H; 7.70 ppm: d: 1 H; 7.85 ppm: dd: 1 H | 14.2 3.30 ppm: s: 3 H; 3.60 ppm: d: 2 H; 4.60 ppm: se: 2 H; 5.95 ppm: dd: 1 H; 6.10 ppm: t: 1 H; 6.20 ppm: d: 1 H; 6.50 ppm: d: 1 H |
| 15 | CH—CH2—N(iPr)(Me) | 15.1 1.30-1.40 ppm: 2d: 6 H; 2.70 ppm: d: 3 H; 3.50-4.00 ppm: m: 3 H; 7.10 ppm: t: 1 H; 7.20-7.30 ppm: m: 1 H; 7.80-8.00 ppm: m: 2 H. | 15.2 |

TABLE 1-continued

Preparations of compounds of formula (III).

| Preparations | $CR_5R_6$ | X = $NO_2$ (IV) NMR | X = $NH_2$ (III) NMR |
|---|---|---|---|
| 16 | CH—CO—NH—NHBoc | 16.1<br>1.40 ppm: s: 9 H;<br>6.70 ppm: s: 1 H;<br>7.20 ppm: d: 1 H;<br>7.80 ppm: d: 1 H;<br>7.95 ppm: dd: 1 H;<br>9.00 ppm: s: 1 H;<br>10.60 ppm: s: 1 H. | 16.2<br>1.40 ppm: s: 9 H;<br>4.70 ppm: se: 2 H;<br>6.05 ppm: dd: 1 H;<br>6.30 ppm: d + s: 2 H; 6.65 ppm: d: 1 H<br>8.90 ppm: s: 1 H;<br>16.20 ppm: s: 1 H. |
| 17 | C—CH₂CH₂—OH<br>\|<br>Me | 17.1<br>1.60 ppm: s: 3 H;<br>2.15 ppm: t: 2 H;<br>3.60 ppm: qd: 2 H;<br>4.60 ppm: t: 1 H;<br>7.00 ppm: d: 1 H;<br>7.70 ppm: d: 1 H;<br>7.85 ppm: dd: 1 H. | 17.2<br>1.50 ppm: s: 3 H;<br>2.00 ppm: t: 2 H;<br>3.55 ppm: qd: 2 H;<br>4.50 ppm: t: 1 H;<br>4.60 ppm: se: 2 H;<br>5.90 ppm: dd: 1 H;<br>6.10 ppm: d: 1 H;<br>6.50 ppm: d: 1 H. |
| 21 | CH—CH₂—N(Me)—C(=O)—O—C(CH₃)₃ | 21.5<br>1.35 ppm: s: 9 H;<br>2.85 ppm: se: 3 H;<br>3.70 ppm: d: 2 H;<br>6.60 ppm: te: 1 H;<br>7.10 ppm: d: 1 H;<br>7.70 ppm: d: 1 H;<br>7.85 ppm: dd: 1 H. | 21.6<br>1.40 ppm: s: 9 H;<br>2.80 ppm: se: 3 H;<br>3.50 ppm: d: 2 H;<br>4.70 ppm: s: 2 H;<br>5.95 ppm: dd: 1 H;<br>6.10-6.20 ppm: m: 1 H;<br>6.20 ppm: d: 1 H;<br>6.50 ppm: d: 1 H. |
| 22 | C(piperidine-N-Boc) | 22.4<br>1.40 ppm: s: 9 H;<br>2.00 ppm: te: 4 H;<br>3.55 ppm: te: 4 H;<br>7.10 ppm: d: 1 H;<br>7.75 ppm: d: 1 H;<br>7.90 ppm: dd: 1 H. | |
| 23 | CH—CH₂N((CH₂)₂OH)₂ | 23.2<br>2.65 ppm: t: 4 H;<br>3.05 ppm: d: 2 H;<br>3.40 ppm: t: 4 H;<br>4.35 ppm: se: 2 H;<br>6.50 ppm: t: 1 H;<br>7.05 ppm: d: 1 H;<br>7.70 ppm: d: 1 H;<br>7.85 ppm: dd: 1 H. | |
| 24 | CH—CH₂CH₂-NH—Boc | 24.7<br>1.35 ppm: s: 9 H;<br>2.10 ppm: qd: 2 H;<br>3.10 ppm: qd: 2 H;<br>6.50 ppm: t: 1 H;<br>6.95 ppm: t: 1 H;<br>7.10 ppm: d: 1 H;<br>7.70 ppm: d: 1 H;<br>7.90 ppm: dd: 1 H. | 24.8<br>1.35 ppm: s: 9 H;<br>1.95 ppm: qd: 2 H;<br>3.10 ppm: qd: 2 H;<br>4.70 ppm: se: 2 H;<br>5.90-6.05 ppm: mt: 2 H;<br>6.15 ppm: d: 1 H;<br>6.50 ppm: d: 1 H;<br>6.90 ppm: t: 1 H. |

Preparation 18

18.1 ((7-Nitro-2,3-dihydro-1,4-benzodioxin-2-yl)methyl)diethylamine hydrochloride 800 µl of diethylamine was added to 1.50 g of 7-nitro-2,3-dihydro-1,4-benzodioxin-2-yl methanesulphonate, described in International patent application WO 01/021 577, in 30 ml of DMF, and heated to 80° C., then 3 times 800 µl of diethylamine were added at 12 hour intervals. After 48 hours, the reaction medium was evaporated to dryness; the residue was taken up in 100 ml of AcOEt then 5 ml of 4N NaOH; the organic phase was decanted, washed with water then with saturated NaCl; after drying and evaporating off the AcOEt, the residue was taken up in 20 ml of AcOEt then 50 ml of 0.5N HCl and stirred then decanted; the aqueous phase was evaporated to dryness and the residue was triturated in ether, filtered and dried. m=0.95 g, MP=192-194° C.

18.2 7-Amino-2,3-dihydro-1,4-benzodioxin-2-yl)methyl)diethylamine 3.05 g of powdered zinc was added to 0.94 g of the nitro derivative obtained in the preceding step in suspension in 40 ml of THF. After cooling to 0° C., 3.1 ml of acetic acid was added over 20 minutes; after 10 minutes the ice bath was removed and stirring was continued for 2 hours. The solid was filtered, washed with THF then with a little methanol. The filtrate was evaporated to dryness, taken up in ethyl acetate, water was added and the pH was brought to 8 using 10N NaOH; the precipitate formed was eliminated by filtration, washed with AcOEt; the filtrate was decanted, washed with saturated NaCl, dried and evaporated; a brown oil was obtained. m=0.51 g.

The compounds of formula (III) and intermediates of formula (IV), all benzodioxine derivatives, were prepared in the racemic form and are characterized in Table 2 below:

The numbers of the compounds shown relate to those given in Table 3 below which illustrates the chemical structures and physical properties of some compounds of the invention. When they contain an asymmetric carbon, these compounds were obtained in the racemic form.

EXAMPLE 1

Compound N° 2

Methyl 5-((7-(((tert-butylamino)carbonyl)amino)-6-(2,6-dichlorophenyl)pyrido[2,3-d]pyrimidin-2-yl)amino)-1,3-benzodioxole-2-carboxylate A mixture of 0.97 g of the compound from preparation 2.2 and 1.40 g of the compound from preparation 1 was heated to reflux in 15 ml of THF. After 6 hours, the reaction medium was concentrated under vacuum. The product was purified by silica chromatography with AcOEt/toluene (2/3) then re-chromatographed with 98/2 CHCl3/MeOH. 0.45 g of a yellow solid was obtained which was identified by mass spectrometry. MH$^+$=583.

TABLE 2

Preparations of compounds of formula (III)

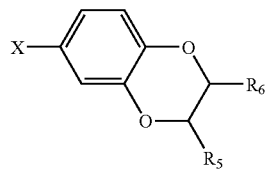

| Preparations | R$_5$ | R$_6$ | X = NO$_2$ (IV), HCl NMR | X = NH$_2$ (III) NMR |
|---|---|---|---|---|
| 18 | CH$_2$—NEt$_2$ | H | 18.1<br>1.00-1.10 ppm: m: 6 H; 3.00-3.40 ppm: m: 6 H; 4.00-4.50 ppm: m: 2 H; 4.80-4.95 ppm: m: 1 H; 7.10 ppm: d: 1 H; 7.65-7.80 ppm: m: 2 H | 18.2<br>1.00 ppm: t: 6 H; 2.45-2.65 ppm: m: 6 H; 3.80-4.20 ppm: m: 3 H; 4.70 ppm: se: 2 H; 6.05-6.20 ppm: m: 2 H; 6.60 ppm: d: 1 H |
| 19 | CH$_2$—N(piperazinyl)N—CH$_3$ | H | 19.1<br>2.85 ppm: s: 3 H; 3.30-3.80 ppm: m: 10 H; 4.15-4.50 ppm: m: 2 H; 4.90-5.10 ppm: m: 1 H; 7.15 ppm: d: 1 H; 7.75-7.90 ppm: m: 2 H | 19.2<br>2.15 ppm: s: 3 H; 2.30-2.60 ppm: m: 10 H; 3.70-4.30 ppm: m: 3 H; 4.60 ppm: se: 2 H; 6.00-6.10 ppm: m: 2 H; 6.50 ppm: d: 1 H. |
| 20 | H | CH$_2$—NEt$_2$ | 20.1<br>1.20-1.30 ppm: m: 6 H; 3.15-3.60 ppm: m: 6 H; 4.10-4.60 ppm: m: 2 H; 5.05 ppm: te: 1 H; 7.15 ppm: d: 1 H; 7.75-7.90 ppm: m: 2 H | 20.2<br>0.90 ppm: t: 6 H; 2.40-2.60 ppm: m: 6 H; 3.75-4.25 ppm: m: 3 H; 4.60 ppm: se: 2 H; 5.95-6.10 ppm: m: 2 H; 6.50 ppm: d: 1 H. |

EXAMPLE 2

Compound N° 4

5-((7-(((Tert-butylamino)carbonyl)amino)-6-(2,6-dichlorophenyl)pyrido[2,3-d]pyrimidin-2-yl)amino)-1,3-benzodioxole-2-carboxylic acid 0.3 ml of 2N sodium hydroxide was added to 0.25 g of the ester obtained in the above example in 10 ml of methanol. After 1 hour 10 minutes of stirring at ambient temperature, the reaction medium was diluted with AcOEt+H2O and the pH was brought to 4 using 1N HCl. The organic phase was decanted, washed with H2O then saturated NaCl, dried and evaporated off. The solid yellow residue was taken up in ether, triturated, filtered and dried. 205 mg of the product was obtained, identified by mass spectrometry. $MH^+$=569.

EXAMPLE 3

Compound N° 3

5-((7-(((tert-Butylamino)carbonyl)amino)-6-(2,6-dichlorophenyl)pyrido[2,3-d]pyrimidin-2-yl)amino)-1,3-benzodioxole-2-carboxamide A mixture of 0.62 g of the compound from preparation 3.2 and 1.40 g of the sulphone derivative from preparation 1 was heated to reflux in 20 ml of THF. After 3 hours, the reaction medium was concentrated under vacuum, then the residue was chromatographed on silica with 97/3 v/v CHCl3/MeOH. 315 mg of a yellow solid was obtained, identified by mass spectrometry. $MH^+$=568.

EXAMPLE 4

Compound N° 9 SSR 105451

N-(Tert-butyl)-N'-(6-(2,6-dichlorophenyl)-2-((2-hydroxymethyl)-1,3-benzodioxol-5-yl)amino)pyrido[2,3-d]pyrimidin-7-yl)urea 43 μl of concentrated HCl was added to a mixture of 350 mg of the compound from preparation 4.2 and 937 mg of the compound from preparation 1 in 15 ml of EtOH; it was heated to 55° C. for 6 hours. The reaction medium was concentrated under vacuum, then the residue was chromatographed on silica; 490 mg of a yellow solid was obtained and identified by mass spectrometry. $MH^+$=555.

EXAMPLE 5

Compound N° 6 SSR 104788

5-((7-(((Tert-butylamino)carbonyl)amino)-6-(2,6-dichlorophenyl)pyrido[2,3-d]pyrimidin-2-yl)amino)-1,3-benzodioxole-2-carbonitrile 50 μl of concentrated HCl was added to 1.00 g of the compound from preparation 1 and 450 mg of the compound from preparation 9.2 in 15 ml of EtOH, then brought to a gentle reflux. After 1½ hours, the reaction medium was concentrated under vacuum. The residue was chromatographed on silica with CHCl3/AcOEt (90/10, v/v). 465 mg of a yellow solid was obtained, identified by mass spectrometry. $MH^+$=550.

EXAMPLE 6

Compound N° 12 SSR 107159

N-(2-((Aminomethyl)-1,3-benzodioxol-5-yl)amino)-6-(2,6-dichlorophenyl)pyrido[2,3-d]pyrimidin-7-yl)-N'-(tert-butyl)urea 1.9 ml of 1M LiAlH4 solution in THF was added to 530 mg of the nitrile derivative of the preceding example dissolved in 25 ml of THF, at −10° C. over 30 minutes. 15 minutes after addition was complete, 1.5 ml of AcOEt then 10 ml of a saturated NH4Cl solution was added and the temperature was allowed to rise. After dilution with AcOEt, it was washed with water then with saturated NaCl. After drying, the organic phase was concentrated under vacuum and the residue was chromatographed on silica with CHCl3/MeOH (95/5; v/v). 165 mg of a yellow solid was obtained which was identified by mass spectrometry. $MH^+$=554.

EXAMPLE 7

Compound N° 19 SSR 109194

Tert-butyl 2-((5-((7-(((tert-butylamino)carbonyl)amino)-6-(2,6-dichlorophenyl)pyrido[2,3-d]pyrimidin-2-yl)amino)-1,3-benzodioxol-2-yl)carbonyl)hydrazine carboxylate.

0.025 ml of concentrated HCl was added to 0.645 g of the product obtained in preparation 1 and 0.63 g of the product obtained in preparation 16.2 in 25 ml of ethanol, then stirred for 5 hours at 70° C. The reaction medium was evaporated and the residue was taken up in CHCl3 then washed with water, a saturated NaHCO3 solution, water, saturated NaCl, then dried and evaporated under vacuum; the residue was chromatographed on silica. 450 mg of a yellow solid was obtained and was identified by mass spectrometry.
$MH^+$=683.

EXAMPLE 8

Compound N° 20 SSR 109195

N-(tert-Butyl)-N'-(6-(2,6-dichlorophenyl)-2-((2-hydrazinocarbonyl)-1,3-benzodioxol-5-yl)amino)pyrido[2,3-d]pyrimidin-7-yl)urea 360 mg of the compound from the preceding example was stirred for 45 minutes in a mixture of 4 ml of CH2Cl2 and 14 ml of TFA; the reaction medium was evaporated under vacuum; the residue was taken up in CHCl3 and washed with H2O, 15% Na2CO3 in water, H2O, and a saturated NaCl solution; after drying, the chloroform was evaporated under vacuum then the residue was triturated in ether, filtered and dried. 225 mg of yellow solid was obtained. $MH^+$=583.

EXAMPLE 9

Compound N° 34

431 mg of compound N° 33 was stirred for 30 minutes at ambient temperature in 5 ml of DCM and 5 ml of TFA. After evaporation, the residue was taken up in a chloroform/water mixture and the pH was brought to 9 by adding an aqueous 15% Na2CO3 solution. The organic phase was decanted, washed with water then with a saturated NaCl solution, dried and concentrated under reduced pressure. 116 mg of a solid was obtained. [M+H]$^+$=568

EXAMPLE 10

Compound N° 35

Step 1:

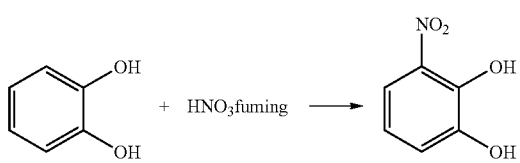

Step carried out in accordance with the operating protocol described in J. Organometall. Chem. 1996, 507, 1-21.

Step 2:

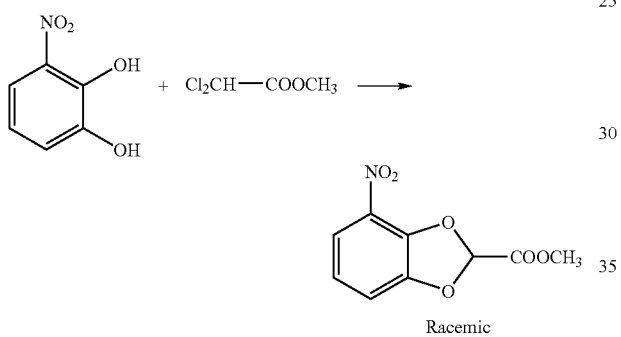

Racemic

Step carried out in accordance with J. Med. Chem. 1988, 31, 84-91.

Step 3:

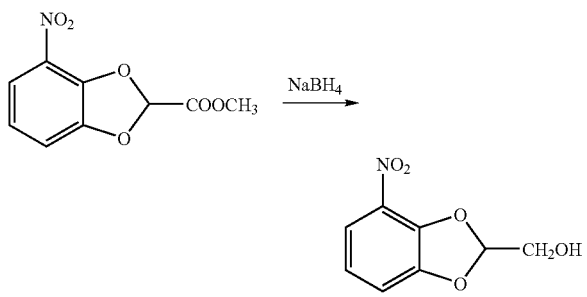

800 mg of sodium borohydride was added to 2.91 g of the product obtained in the preceding step in 40 ml of methanol, at 8° C. over 35 minutes. After 50 minutes, the reaction medium was poured onto 150 ml of water/ice plus 400 ml of ethyl acetate; after stirring for 5 minutes, decanting, washing the organic phase with a 5% KHSO4/K2SO4 solution, water, a saturated NaCl solution, drying and evaporating the organic phase, a brown solid was isolated.

m=2.25 g.

Step 4:

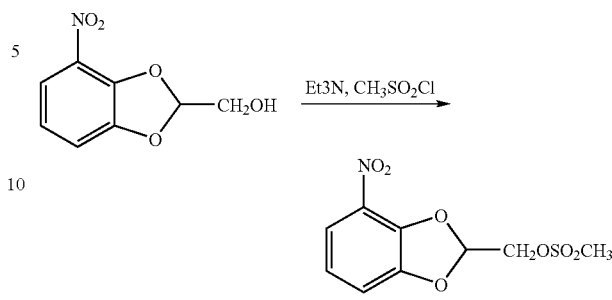

1.43 g of triethylamine was added to 2.24 g of the preceding alcohol in 60 ml of DCM, followed by 1.67 g of methane sulphonyl chloride over 25 minutes. After 45 minutes, the reaction medium was diluted with 100 ml of DCM; the organic phase was washed twice with ice water and once with a saturated NaCl solution, then dried and concentrated under vacuum. A brown solid was obtained. m=3.01 g.

Step 5

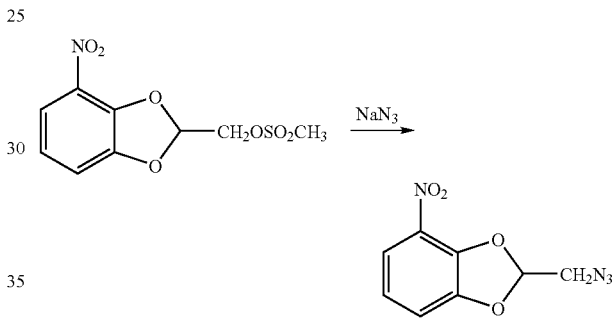

A mixture of 3.0 g of the product obtained in step 4 and 1.82 g of sodium nitride was heated for 7 h 30 mins in 20 ml of DMF at 65° C. The reaction medium was then poured onto 75 ml of ice water and 300 ml of ether. The organic phase was isolated and washed several times with water then with a saturated NaCl solution. The organic phase was dried and concentrated under vacuum to produce a brown solid. m=2.20 g.

Step 6:

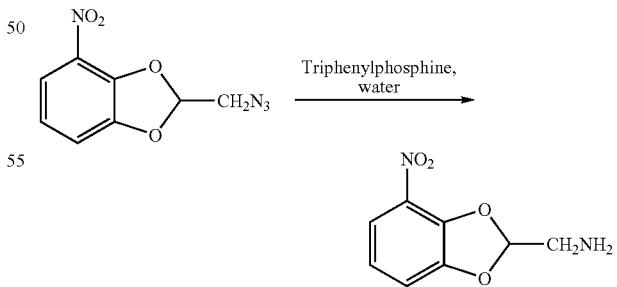

4.33 g of triphenylphosphine was added to 2.19 g of the product obtained in step 5, dissolved in 50 ml of ethyl acetate, over 15 minutes then, after 10 minutes, 1.8 ml of water was added over 2 minutes. The reaction medium was stirred for 1 h 40 mins at 60° C. then was diluted with 150 ml of ethyl acetate. The solution obtained was washed twice with water, once with a saturated NaCl solution, dried and evaporated. The residue from evaporation was dissolved in a mixture of 50 ml of ethyl acetate and 50 ml of ethyl ether and extracted twice with 50 ml of 1N HCl. The acid aqueous phases were combined and extracted using a mixture of 25 ml of ethyl acetate and 25 ml of ethyl ether, then brought into contact with 300 ml of ethyl acetate and the pH was brought to 9 with 10N NaOH. After decanting, the organic phase was washed with water, a saturated NaHCO3 solution, water, and then a saturated NaCl solution. The residual organic phase was dried then concentrated under vacuum. An oil was obtained. m=1.40 g.

Step 7:

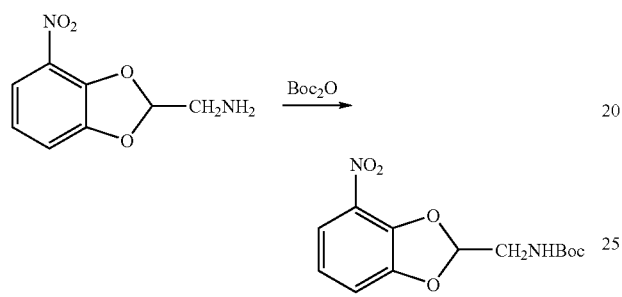

0.35 g of triethylamine then 1.75 g of Boc2O were added at 5° C. to 1.39 g of the amine obtained in step 6 in 35 ml of DCM over a period of 10 minutes. After stirring overnight at ambient temperature, the reaction medium was diluted with 150 ml of DCM, washed with water, a 5% KHSO4/K2SO4 solution, water, then with a saturated NaCl solution. After drying and evaporating off the DCM, the solid obtained was dissolved in a minimum of ethyl ether then heptane was added to total precipitation. A solid was obtained. m=1.90 g.

NMR: 1.30 ppm:s:9H; 3.40-3.55 ppm:mt:2H; 6.55 ppm:t: 1H; 7.00 ppm:t:1H; 7.15-7.30 ppm:mt:2H; 7.55 ppm:d:1H.

Step 8:

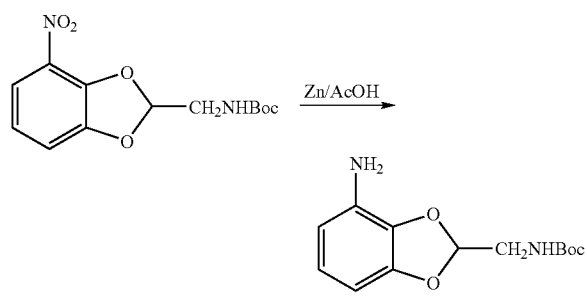

1.96 g of powdered zinc was added to 0.60 g of the product obtained in step 7 in 25 ml of THF then, at −3° C., 2 ml of AcOH was added over a period of 25 minutes. When addition was complete, the reaction medium was allowed to return to ambient temperature. After 1 h 15 mins, the reaction medium was filtered, the filtrate was diluted with 150 ml of ethyl acetate and 30 ml of water and the pH was brought to 9 by adding a 15% Na2CO3 solution. After decanting, the organic phase was isolated, washed with a saturated NaHCO3 solution, water, then with a saturated NaCl solution. The organic phase was isolated, dried, and then concentrated under reduced pressure. 0.53 g of a viscous yellow oil was obtained.

NMR: 1.35 ppm:s:9H; 3.30 ppm:mt:2H; 4.80 ppm:s:2H; 6.05 ppm:t:1H; 6.10-6.25 ppm:mt:2H; 6.50 ppm:t:1H; 7.10 ppm:t:1H.

Step 9:

Coupling to Obtain Compound 35 Under Standardized Conditions as Described Above.

EXAMPLE 11

Compound N° 45

1.035 ml of DIPEA then 0.675 g of formamidinylsulphonic acid (H2N—C(═NH)—SO3H) were added to 1 g of compound 12 dissolved in 15 ml of methanol and 2 ml of DMF. After stirring overnight at 25° C., the reaction medium was supplemented with water and the precipitate formed was filtered, washed with water then dried under reduced pressure. The crude product was flash chromatographed on silica gel with a 10% to 50% MeOH gradient in DCM. 170 mg of solid was obtained, transformed into a salt using one mole/mole of H2SO4. MS: MH$^+$=596

EXAMPLE 12

Compound N° 39

Preparation 39.1

0.11 ml of pyridine was added to 555 mg of compound 9 (Example 4) in 10 ml of DCM at 5° C., followed by 0.20 ml of triflic anhydride diluted in 2 ml of DCM over 15 minutes. After 45 minutes, the reaction medium was diluted with 50 ml of DCM, washed in succession with ice water, water, a 5% KHSO4/K2SO4 solution, water, then a saturated NaCl solution. The organic phase was then dried and concentrated under reduced pressure. 593 mg of solid was recovered.

1H NMR: 1.40 ppm: s: 9H; 4.65 ppm: se: 2H; 6.50 ppm: t: 1H; 6.90 ppm: d: 1H; 7.40 ppm: de: 1H; 7.50-7.70 ppm: m: 3H; 8.00 ppm: se: 1H; 8.05 ppm: s: 1H; 8.20 ppm: se: 1H; 9.00 ppm: s: 1H; 10.15 ppm: s: 1H; 10.70 ppm: s: 1H.

Preparation 39.2

0.17 ml of morpholine was added to 579 mg of the compound obtained in step 39.1 in 10 ml of DCM. The reaction medium was stirred for 3 h 30 mins at ambient temperature, and then evaporated under reduced pressure. The residue was purified by flash chromatography on silica gel with a gradient of 0 to 20% AcOEt in DCM. 300 mg of a yellow powder was obtained. MS: MH$^+$=624.

EXAMPLE 13

Compounds N°s 40-43

Compounds 40 to 43 were prepared in the same manner as compound 39 cited in Example 12, using the compound obtained in step 39.1 and replacing the morpholine in step 39.2 by tert-butylamine, 1-Boc-piperazine; cyclopropylamine cis-2,6-dimethylpiperidine respectively.

EXAMPLE 14

Compound N° 44

Compound N° 44 was obtained by de-protecting compound 41 obtained in Example 13 using the method described above employing TFA.

EXAMPLE 15

Compounds N°s 46-48

Compound 12 was reacted with an acid in its activated form, for example the anhydride, acid chloride, acid+coupling agent, for example DCCI, BOP.

Thus, compounds 46 to 48 were produced by reacting compound 12 with acetic anhydride, benzoyl chloride and cyclopropanecarbonyl chloride respectively.

EXAMPLE 16

Compound N° 49

444 mg of compound 12 in 12 ml of acetonitrile was cooled to 5° C. 0.14 ml of triethylamine was added followed by 0.075 ml of methanesulphonyl chloride. After stirring for 40 minutes at 25° C., the reaction medium was taken up in AcOEt. The organic phase was washed with water, washed with a saturated NaCl solution, dried and evaporated under reduced pressure. The residue was purified by flash chromatography on silica gel with a gradient of 0 to 5% methanol in chloroform. 220 mg of solid was obtained. MS: MH$^+$=632.

EXAMPLE 17

Compound N° 50

40 mg of tertiobutylamine, 71 mg of diisopropylamine and 176 mg of O-(1H-benzotriazol-1-yl)-N,N,N',N'-tetramethyluronium tetrafluoroborate (TBTU) were added to 284 mg of compound 4 (Example 2) in 5 ml of DMF. The reaction medium was stirred for 1 hour at 25° C. then diluted with AcOEt. The organic phase was washed successively with water, a saturated NaHCO3 solution, water, and then a saturated NaCl solution. The organic phase was dried, evaporated under reduced pressure, and the residue was purified by flash chromatography on silica gel with a gradient of 0 to 5% methanol in DCM. 196 mg of a yellow solid was obtained. MS: MH$^+$=624.

EXAMPLE 18

Compounds Nos 51-54

Compounds 51 to 54 were prepared in the same manner as described for compound 50 starting from compound 4 and replacing the tertiobutylamine with cyclopropylamine, pyrrolidine, N-isopropyl-methylamine and methylamine respectively.

EXAMPLE 19

Compound N° 62

819 mg of the compound described in preparation 1 and 0.314 mg of 6-amino-2,3-dihydro-benzo[b]furan, which may be prepared in accordance with Eur. J. Med. Chem. Chimica Therapeutica, 1977, Vol. 12, 231-235, were stirred for 3 hours at 70° C. in 25 ml of absolute alcohol containing 0.02 ml of concentrated HCl. After cooling, the precipitate was filtered, washed with tepid MeOH then with Et2O. 637 mg of a yellow solid melting at 197° C. was obtained. MS: MH$^+$=523.

EXAMPLE 20

Compound N° 69

Step 1

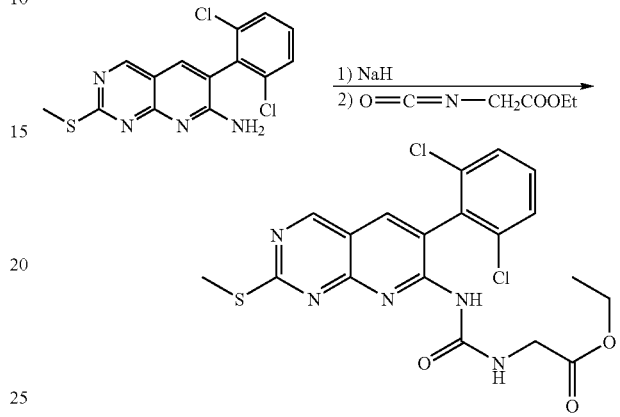

432 mg of 60% NaH was added over 10 minutes to 3.0 g of the product obtained in step 1.4 in 25 ml of DMF. After stirring for 30 minutes, 1.40 g of ethyl isocyanatoacetate was added over 10 minutes then the reaction medium was stirred for 3 h 30 mins at ambient temperature. The reaction medium was extracted with AcOEt, washed successively with water, a 5% KHSO4/K2SO4 solution, water, and with a saturated NaCl solution. The organic phase was dried, concentrated under vacuum and the crude product obtained was purified by silica gel chromatography, eluting with 85/15 v/v CHCl3/AcOEt to obtain 1.52 g of the expected product.

Step 2

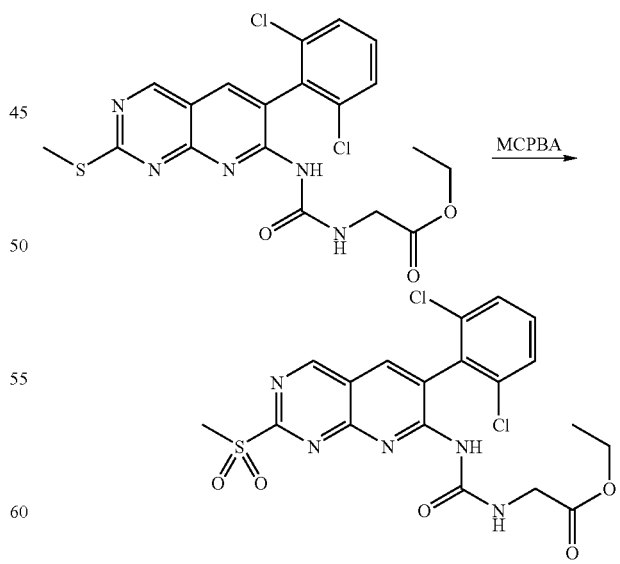

The product obtained in step 1 was oxidized with metachloroperbenzoic acid (MCPBA) using the method described in preparation 1.6. 900 mg of the expected product was obtained in the form of a beige solid.

Step 3

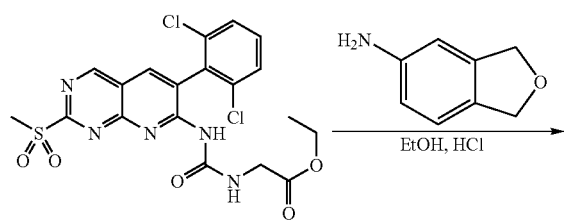

798 mg of the product from step 2 and 295 mg of 1,3-dihydro-2-benzofuran-5-amine were heated at 65° C. for 6 hours in the presence of 15 ml of EtOH and 0.06 ml of concentrated HCl. The reaction medium was diluted with CHCl3 and water, then the pH of the aqueous phase was brought to 9 by adding a saturated NaHCO3 solution. After decanting, the organic phase was isolated, washed with water and then with a saturated NaCl solution, dried and concentrated under reduced pressure. The product was crystallized in AcOEt. 0.67 g of a yellow solid was obtained.

Step 4

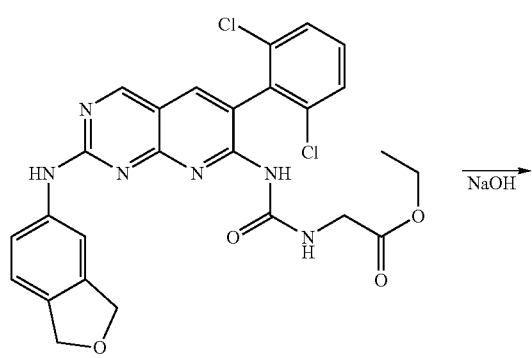

0.66 g of the ester obtained in step 3 in 25 ml of ethanol and 2 ml of DMF were treated with 1.5 ml of 2N NaOH for 5 hours. The reaction medium was diluted with CHCl3, and then the pH was brought to 4 with 1N HCl and decanted. The organic phase was isolated, washed with water then with a saturated NaCl solution, dried and concentrated under reduced pressure to obtain 0.61 g of a yellow powder.

Step 5

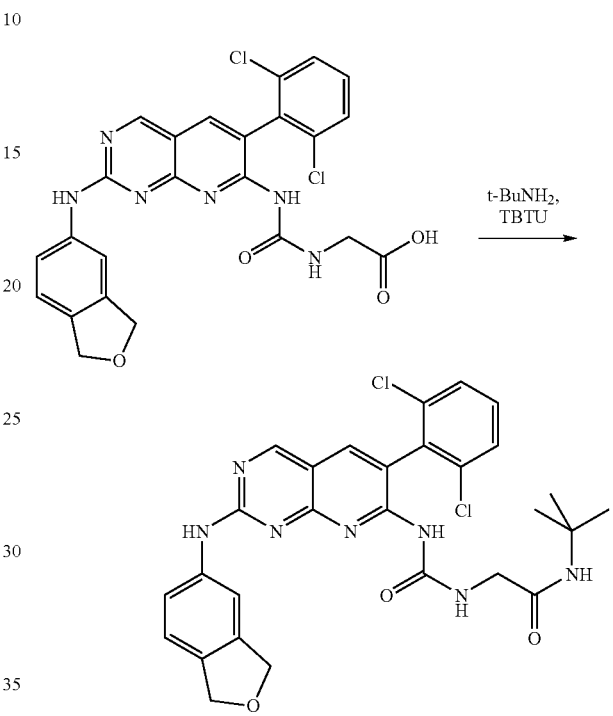

105 mg of the product obtained in step 4, 16 mg of tert-butylamine, 28 mg of DIPEA (diisopropylethylamine) and 70 mg of TBTU were stirred for 1 h 15 mins in 2.5 ml of DMF. The reaction medium was then extracted with CHCl3, the organic phase was washed successively with water, a 5% KHSO4/K2SO4 solution, a saturated NaCl solution and then was dried and evaporated under reduced pressure. The crude product was purified by silica chromatography, eluting with CHCl3/MeOH, 94/6 v/v. 90 mg of the expected product was obtained in the form of a yellow solid. MS: MH$^+$=580.

EXAMPLE 21

Compounds 31 and 32

The enantiomers of compound 12, prepared in Example 6, were separated by chiral stationary phase chromatography as follows:

| | |
|---|---|
| Technique | Berger Prep SFC |
| Detection | UV 230 nm |
| Stationary phase | Chiralpack AD-H 250 × 21 mm (5 μm) |
| Mobile phase | 60%/40% CO$_2$/(Ethanol + 0.5% isopropylamine) |
| Flow rate | 50 ml/minute |
| Pressure | 100 bar |
| Number of injections | Stacking, 350 injections of 28 mg |

Starting from 10 g of the racemic mixture, following separation, 4.147 g of the dextrogyratory enantiomer (compound 31) and 4.077 g of the laevogyratory enantiomer (compound 32) were obtained.

Tables 3 and 4 below illustrate the chemical structures and physical properties of some examples in accordance with the invention. In these tables, Me, Et, iPr and tBu respectively represent methyl, ethyl, isopropyl and tert-butyl groups, and Boc represents the tert-butoxycarbonyl group. Unless otherwise indicated, products comprising an asymmetric carbon atom were obtained in the racemic form.

TABLE 3

(I)

| Compounds | Ar₁ | X | NMR characterization |
|---|---|---|---|
| 1 | benzodioxole-CH₂—NEt₂ | Cl | 0.90 ppm: t: 6 H; 1.40 ppm: s: 9 H; 2.55 ppm: qd: 4 H; 2.80 ppm: de: 2 H; 6.15 ppm: t: 1 H; 6.70 ppm: d: 1 H; 7.20 ppm: de: 1 H; 7.40-7.65 ppm: m: 3 H; 7.95 ppm: se: 1 H; 8.00 ppm: s: 1 H; 8.10 ppm: s: 1 H; 9.00 ppm: s: 1 H; 10.05 ppm: s: 1 H; 10.60 ppm: s: 1 H. |
| 2 | benzodioxole-COOMe | Cl | 1.40 ppm: s: 9 H; 3.75 ppm: s: 3 H; 6.65 ppm: s: 1 H; 6.90 ppm: d: 1 H; 7.25-7.65 ppm: m: 4 H; 8.00 ppm: se: 2 H; 8.20 ppm: s: 1 H; 9.00 ppm: s: 1 H; 10.15 ppm: s: 1 H; 10.65 s: 1 H. |
| 3 | benzodioxole-CONH₂ | Cl | 1.35 ppm: s: 9 H; 6.20 ppm: s: 1 H; 6.75 ppm: d: 1 H; 7.25-8.05 ppm: m: 9 H; 9.00 ppm: s: 1 H; 10.00 ppm: s: 1 H; 10.55 ppm: s: 1 H. |
| 4 | benzodioxole-COOH | Cl | 1.45 ppm: s: 9 H; 6.60 ppm: s: 1 H; 7.00 ppm: d: 1 H; 7.40-7.75 ppm: m: 4 H; 8.10 ppm: s: 1 H; 8.15 ppm: s: 1 H; 8.25 ppm: s: 1 H; 9.15 ppm: s: 1 H; 10.20 ppm: s: 1 H; 10.75 ppm: s: 1 H; 14 ppm: se: 1 H |
| 5 | benzodioxole-CONMe₂ | Cl | 1.45 ppm: s: 9 H; 2.95 ppm: s: 3 H; 3.15 ppm: s: 3 H; 6.90 ppm: d: 1 H; 7.05 ppm: s: 1 H; 7.35 ppm: de: 1 H; 7.50-7.75 ppm: m: 3 H; 8.05 ppm: se: 1 H; 8.10 ppm: s: 1 H; 8.20 ppm: s: 1 H; 9.15 ppm: s: 1 H; 10.20 ppm: s: 1 H; 10.70 ppm: s: 1 H. |
| 6 | benzodioxole-CN | Cl | 1.40 ppm: s: 9 H; 7.10 ppm: d: 1 H; 7.35-7.65 ppm: m: 5 H; 8.05 ppm: s: 1 H; 8.20 ppm: s: 1 H; 8.30 ppm: s: 1 H; 9.05 ppm: s: 1 H; 10.25 ppm: s: 1 H; 10.75 ppm: s: 1 H. |

TABLE 3-continued (I)

| Compounds | Ar₁ | X | NMR characterization |
|---|---|---|---|
| 7 | 5-methyl-benzo[1,3]dioxol-2-yl-CONHEt | Cl | 1.05 ppm: t: 3 H; 1.40 ppm: s: 9 H; 3.10 ppm: qt: 2 H; 6.30 ppm: s: 1 H; 6.90 ppm: d: 1 H; 7.30-7.65 ppm: m: 4 H; 7.85 ppm: s: 1 H; 8.05 ppm: s: 1 H; 8.15 ppm: s: 1 H; 8.55 ppm: t: 1 H; 9.05 ppm: s: 1 H; 10.10 ppm: s: 1 H; 10.65 ppm: s: 1 H. |
| 8 | 5-methyl-benzo[1,3]dioxol-2-yl-(CONH₂)₂ | Cl | 1.45 ppm: s: 9 H; 6.95 ppm: d: 1 H; 7.50-7.90 ppm: m: 9 H; 8.05 ppm: s: 1 H; 8.10 ppm: s: 1 H; 9.10 ppm: s: 1 H; 10.10 ppm: s: 1 H; 10.60 ppm: s: 1 H. |
| 9 | 5-methyl-benzo[1,3]dioxol-2-yl-CH₂OH | Cl | 1.50 ppm: s: 9 H; 3.80 ppm: m: 2 H; 5.35 ppm: t: 1 H; 6.25 ppm: t: 1 H; 6.85 ppm: d: 1 H; 7.40-8.25 ppm: m: 7 H; 9.10 ppm: s: 1 H; 10.15 ppm: s: 1 H; 10.75 ppm: s: 1 H. |
| 10 | 5-methyl-benzo[1,3]dioxol-2-yl-(CH₂OH)₂ | Cl | 1.40 ppm: s: 9 H; 3.60 ppm: d: 4 H; 5.15 ppm: t: 2 H; 6.60 ppm: d: 1 H; 7.30-7.60 ppm: m: 5 H; 7.95 ppm: s: 1 H; 8.05 ppm: s: 1 H; 9.00 ppm: s: 1 H; 9.95 ppm: s: 1 H; 10.55 ppm: s: 1 H. |
| 11 | 5-methyl-benzo[1,3]dioxol-2-yl-CH₂-N(4-Me-piperazinyl) | Cl | 1.40 ppm: s: 9 H; 2.80 ppm: s: 3 H; 3.20-3.70 ppm: m: 10 H; 6.65 ppm: te: 1 H; 6.95 ppm: d: 1 H; 7.35 ppm: de: 1 H; 7.50-7.75 ppm: m: 3 H; 7.95 ppm: se: 1 H; 8.25 ppm: s: 1 H; 9.15 ppm: s: 1 H; 10.40 ppm: se: 2 H; 11.50 ppm: se: 1 H. |
| 12 | 5-methyl-benzo[1,3]dioxol-2-yl-CH₂NH₂ | Cl | 1.40 ppm: s: 9 H; 1.55 ppm: se: 2 H; 2.90 ppm: d: 2 H; 6.10 ppm: t: 1 H; 6.75 ppm: d: 1 H; 7.30 ppm: de: 1 H; 7.45-7.70 ppm: m: 3 H; 7.85 ppm: se: 1 H; 8.05 ppm: s: 1 H; 8.10 ppm: se: 1 H; 9.00 ppm: s: 1 H; 10.00 ppm: s: 1 H; 10.70 ppm: s: 1 H. |
| 13 | 5-methyl-benzo[1,3]dioxol-2-yl-CONHNMe₂ | Cl | 1.40 ppm: s: 9 H; 2.45 ppm: s: 6 H; 6.20 ppm: s: 1 H; 6.80-6.95 ppm: m: 2 H; 7.30-7.70 ppm: m: 4 H; 7.85-8.15 ppm: m: 3 H; 9.00 ppm: s: 1 H; 10.10 ppm: s: 1 H; 10.70 ppm: s: 1 H. |

TABLE 3-continued (I)

| Compounds | Ar₁ | X | NMR characterization |
|---|---|---|---|
| 14 | (6-methyl-2-methyl-1,3-benzodioxol-2-yl)-CH₂-CH₂-NEt₂ | Cl | 0.95 ppm: t: 6 H; 1.40 ppm: s: 9 H; 1.60 ppm: s: 3 H; 1.95-2.05 ppm: m: 2 H; 2.35-2.70 ppm: m: 6 H; 6.70 ppm: d: 1 H; 7.20 ppm: de: 1 H; 7.40-7.70 ppm: m: 3 H; 7.90 ppm: se: 1 H; 8.00 ppm: s: 1 H; 8.10 ppm: s: 1 H; 9.00 ppm: s: 1 H; 10.00 ppm: s: 1 H; 10.60 ppm: s: 1 H. |
| 15 | (6-methyl-1,3-benzodioxol-2-yl)-CH₂OCH₃ | Cl | 1.40 ppm: s: 9 H; 3.40 ppm: s: 3 H; 3.65 ppm: d: 2 H; 6.30 ppm: t: 1 H; 6.75 ppm: d: 1 H; 7.30 ppm: dd: 1 H; 7.45-7.60 ppm: m: 3 H; 7.85 ppm: s: 1 H; 8.05 ppm: s: 1 H; 8.10 ppm: s: 1 H; 9.00 ppm: s: 1 H; 10.00 ppm: s: 1 H; 10.70 ppm: s: 1 H. |
| 16 | (7-methyl-2,3-dihydro-1,4-benzodioxin-2-yl)-CH₂-NEt₂ | Cl | 0.85 ppm: t: 6 H; 1.35 ppm: s: 9 H; 2.40-2.60 ppm: m: 6 H; 3.80-4.20 ppm: m: 3 H; 6.65 ppm: d: 1 H; 7.15 ppm: de: 1 H; 7.40-7.60 ppm: m: 3 H; 7.80 ppm: se: 1 H; 7.95 ppm: s: 1 H; 8.00 ppm: se: 1 H; 8.95 ppm: s: 1 H; 9.95 ppm: s: 1 H; 10.50 ppm: s: 1 H. |
| 17 | (7-methyl-2,3-dihydro-1,4-benzodioxin-2-yl)-CH₂-N(piperazinyl)-N-Me | Cl | 1.50 ppm: s: 9 H; 2.20 ppm: s: 3 H; 2.40-2.60 ppm: m: 10 H; 3.90-4.40 ppm: m: 3 H; 6.80 ppm: d: 1 H; 7.35 ppm: de: 1 H; 7.55-7.75 ppm: m: 3 H; 8.00 ppm: se: 1 H; 8.10 ppm: s: 1 H; 8.20 ppm: s: 1 H; 9.10 ppm: s: 1 H; 10.10 ppm: s: 1 H; 10.65 ppm: s: 1 H. |
| 18 | (7-methyl-2,3-dihydro-1,4-benzodioxin-3-yl)-CH₂-NEt₂ | Cl | 0.95 ppm: t: 6 H; 1.40 ppm: s: 9 H; 2.40-2.70 ppm: m: 6 H; 3.90-4.35 ppm: m: 3 H; 6.75 ppm: d: 1 H; 7.35-7.65 ppm: m: 4 H; 7.90 ppm: se: 1 H; 8.05 ppm: s: 1 H; 8.10 ppm: s: 1 H; 9.05 ppm: s: 1 H; 10 ppm: s: 1 H; 10.60 ppm: s: 1 H. |
| 19 | (6-methyl-1,3-benzodioxol-2-yl)-CONHNHBoc | Cl | 1.40 ppm: s: 9 H; 1.45 ppm: s: 9 H; 6.45 ppm: s: 1 H; 6.85 ppm: s: 1 H; 7.40-7.70 ppm: m: 4 H; 7.90 ppm: se: 1 H; 8.05 ppm: s: 1 H; 8.15 ppm: s: 1 H; 8.90 ppm: se: 1 H; 9.05 ppm: s: 1 H; 10.10 ppm: s: 1 H; 10.40 ppm: s: 1 H; 10.70 ppm: s: 1 H. |

TABLE 3-continued (I)

| Compounds | Ar₁ | X | NMR characterization |
|---|---|---|---|
| 20 | benzo[1,3]dioxol-2-yl with Me substituent, -CONHNH₂ | Cl | 1.40 ppm: s: 9 H; 4.50 ppm: se: 2 H; 6.45 ppm: s: 1 H; 6.60 ppm: d: 1 H; 7.30-7.70 ppm: m: 4 H; 7.85 ppm: se: 1 H; 8.00 ppm: s: 1 H; 8.10 ppm: s: 1 H; 9.00 ppm: s: 1 H; 9.80 ppm: s: 1 H; 10.10 ppm: s: 1 H; 10.70 ppm: s: 1 H. |
| 21 | benzo[1,3]dioxole with Me substituent | Cl | 1.45 ppm: s: 9 H; 5.00 ppm: s: 4 H; 7.25 ppm: d: 1 H; 7.45-7.75 ppm: m: 4 H; 8.05 ppm: s: 1 H; 8.10 ppm: se: 1 H; 8.35 ppm: se: 1 H; 9.10 ppm: s: 1 H; 10.10 ppm: se: 1 H; 10.70 ppm: se: 1 H. |
| 22 | benzo[1,3]dioxol-2-yl with Me substituent, -CH₂NiPr-Me | Cl | 0.95 ppm: d: 6 H; 1.40 ppm: s: 9 H; 2.25 ppm: s: 3 H; 2.70-2.85 ppm: m: 3 H; 6.20 ppm: t: 1 H; 6.75 ppm: d: 1 H; 7.25 ppm: de: 1 H; 7.45-7.65 ppm: m: 3 H; 7.95 ppm: se: 1 H; 8.05 ppm: s: 1 H; 8.10 ppm: se: 1 H; 9.00 ppm: s: 1 H; 10.10 ppm: se: 1 H; 10.70 ppm: se: 1 H. |
| 23 | benzo[1,3]dioxol-2-yl with Me substituent, -CONHOMe | Cl | 1.45 ppm: s: 9 H; 3.60 ppm: s: 3 H; 6.35 ppm: s: 1 H; 6.75 ppm: d: 1 H; 7.35-7.65 ppm: m: 4 H; 7.90 ppm: se: 1 H; 8.05 ppm: s: 1 H; 8.15 ppm: se: 1 H; 9.00 ppm: s: 1 H; 10.10 ppm: se: 1 H; 10.60 ppm: se: 1 H; 11.90 ppm: se: 1 H. |
| 24 | benzo[1,4]dioxin with Me substituent, -CH₂-N-piperazine-N-Me | Cl | 1.40 ppm: s: 9 H; 2.20-2.60 ppm: m: 13 H; 3.80-4.30 ppm: m: 3 H; 6.75 ppm: d: 1 H; 7.30 ppm: de: 1 H; 7.45-7.70 ppm: m: 3 H; 7.85 ppm: se: 1 H; 8.00 ppm: s: 1 H; 8.10 ppm: se: 1 H; 9.00 ppm: s: 1 H; 10.05 ppm: se: 1 H; 10.70 ppm: se: 1 H. |
| 25 | benzo[1,4]dioxin with Me substituent, -CH₂OH | Cl | 1.45 ppm: s: 9 H; 3.55-3.65 ppm: m: 2 H; 3.90-4.30 ppm: m: 3 H; 5.50 ppm: t: 1 H; 6.75 ppm: d: 1 H; 7.35 ppm: dd: 1 H; 7.45-7.70 ppm: m: 3 H; 7.85 ppm: se: 1 H; 8.05 ppm: s: 1 H; 8.10 ppm: se: 1 H; 9.00 ppm: s: 1 H; 10.00 ppm: se: 1 H; 10.70 ppm: se: 1 H. |

TABLE 3-continued (I)

| Compounds | Ar₁ | X | NMR characterization |
|---|---|---|---|
| 26 | 5-methyl-benzo[1,3]dioxol-2-yl-CH₂–N(4-methylpiperazin-1-yl) | Me | 1.40 ppm: s: 9 H; 2.00 ppm: s: 6 H; 2.20 ppm: s: 3 H; 2.40-2.75 ppm: m: 10 H; 6.25 ppm: t: 1 H; 6.45 ppm: s: 1 H; 6.75 ppm: d: 1 H; 7.15-7.40 ppm: m: 4 H; 7.95 ppm: s: 1 H; 8.05 ppm: se: 1 H; 9.00 ppm: s: 1 H; 10.00 ppm: se: 1 H; 10.50 ppm: se: 1 H. |
| 27 | 6-methyl-4H-benzo[1,3]dioxine | Cl | 1.40 ppm: s: 9 H; 4.80 ppm: s: 2 H; 5.25 ppm: s: 2 H; 6.70 ppm: d: 1 H; 7.45-7.70 ppm: m: 4 H; 7.90-8.10 ppm: m: 3 H; 9.00 ppm: s: 1 H; 10.00 ppm: se: 1 H; 10.50 ppm: se: 1 H. |
| 28 | 7-methyl-4H-benzo[1,3]dioxine | Cl | 1.40 ppm: s: 9 H; 4.80 ppm: s: 2 H; 5.25 ppm: s: 2 H; 6.90 ppm: d: 1 H; 7.40-7.70 ppm: m: 4 H; 7.90 ppm: se: 1 H; 8.05 ppm: s: 1 H; 8.15 ppm: se: 1 H; 9.10 ppm: s: 1 H; 10.20 ppm: se: 1 H; 10.70 ppm: se: 1 H. |
| 29 | 2-(2-hydroxyethyl)-2,5-dimethyl-benzo[1,3]dioxole | Cl | 1.40 ppm: s: 9 H; 1.60 ppm: s: 3 H; 2.05 ppm: t: 2 H; 3.60 ppm: t: 2 H; 3.60 ppm: se: 1 H; 6.70 ppm: d: 1 H; 7.20 ppm: de: 1 H; 7.40-7.70 ppm: m: 3 H; 7.80 ppm: se: 1 H; 8.00 ppm: s: 1 H; 8.20 ppm: se: 1 H; 9.00 ppm: s: 1 H; 10.00 ppm: se: 1 H; 10.70 ppm: se: 1 H. |
| 30 | 5-methyl-benzo[1,3]dioxol-2-yl-CH₂–NH–Boc | Cl | 1.30 ppm: s: 9 H; 1.40 ppm: s: 9 H; 3.30 ppm-3.40 ppm: mt: 2 H; 6.15 ppm: t: 1 H; 6.75 ppm: d: 1 H; 7.15 ppm: t: 1 H; 7.35 ppm: de: 1 H; 7.45-7.65 ppm: m: 3 H; 7.85 ppm: se: 1 H; 8.05 ppm: s: 1 H; 8.15 ppm: se: 1 H; 9.00 ppm: s: 1 H; 10.05 ppm: s: 1 H; 10.65 ppm: s: 1 H. |
| 31 | 5-methyl-benzo[1,3]dioxol-2-yl-CH₂–NH₂<br>Dextrogyratory: $[\alpha]_D = +67.6°$, (C = 0.5; MeOH) | Cl | 1.40 ppm: s: 9 H; 1.55 ppm: se: 2 H; 2.90 ppm: d: 2 H; 6.10 ppm: t: 1 H; 6.75 ppm: d: 1 H; 7.30 ppm de: 1 H; 7.45-7.70 ppm: m: 3 H; 7.85 ppm: se: 1 H; 8.05 ppm: s: 1 H; 8.10 ppm: se: 1 H; 9.00 ppm: s: 1 H; 10.00 ppm: s: 1 H; 10.70 ppm: se: 1 H. |

TABLE 3-continued (I)

Ar₁—NH—[pyrimido-pyridine core]—NH—C(=O)—NH-tBu, with X,X on phenyl ring

| Compounds | Ar₁ | X | NMR characterization |
|---|---|---|---|
| 32 | 5-methyl-benzo[1,3]dioxol-2-yl-CH₂NH₂ (Laevogyratory: $[\alpha]_D = -67$ (C = 0.5; MeOH)) | Cl | 1.40 ppm: s: 9 H; 1.55 ppm: se: 2 H; 2.90 ppm: d: 2 H; 6.10 ppm: t: 1 H; 6.75 ppm: d: 1 H; 7.30 ppm: de: 1 H; 7.45-7.70 ppm: m: 3 H; 7.85 ppm: se: 1 H; 8.05 ppm: s: 1 H; 8.10 ppm: se: 1 H; 9.00 ppm: s: 1 H; 10.00 ppm: s: 1 H; 10.70 ppm: s: 1 H. |
| 33 | 5-methyl-benzo[1,3]dioxol-2-yl-CH₂-N(Me)-C(=O)O-tBu | Cl | 1.35 ppm: s: 9 H; 1.40 ppm: s: 9 H; 2.85 ppm: se: 3 H; 3.60 ppm: d: 2 H; 6.30 ppm: t: 1 H; 6.80 ppm: d: 1 H; 7.30 ppm: de: 1 H; 7.45-7.70 ppm: m: 3 H; 8.00 ppm: se: 1 H; 8.05 ppm: s: 1 H; 8.15 ppm: se: 1 H; 9.00 ppm: s: 1 H; 10.10 ppm: s: 1 H; 10.70 ppm: s: 1 H. |
| 34 | 5-methyl-benzo[1,3]dioxol-2-yl-CH₂-NH-Me | Cl | 1.40 ppm: s: 9 H; 1.80 ppm: se: 1 H; 2.30 ppm: s: 3 H; 2.85 ppm: d: 2 H; 6.20 ppm: t: 1 H; 6.75 ppm: d: 1 H; 7.30 ppm: dd: 1 H; 7.45-7.65 ppm: m: 3 H; 7.85 ppm: se: 1 H; 8.00 ppm: s: 1 H; 8.10 ppm: se: 1 H; 9.00 ppm: s: 1 H; 10.00 ppm: s: 1 H; 10.70 ppm: s: 1 H. |
| 35 | 4-methyl-benzo[1,3]dioxol-2-yl-CH₂-NH-C(=O)O-tBu | Cl | 1.35 ppm: s: 9 H; 1.40 ppm: s: 9 H; 3.25 ppm-3.40 ppm: m: 2 H; 6.25 ppm: t: 1 H; 6.65 ppm-6.80 ppm: mt: 2 H; 7.10 ppm: t: 1 H; 7.50 ppm-7.65 ppm: m: 4 H; 8.05 ppm: s: 1 H; 8.10 ppm: s: 1 H; 9.05 ppm: s: 1 H; 9.20 ppm: s: 1 H; 10.40 ppm: s: 1 H. |
| 36 | 5-methyl-2,2-bis(aminomethyl)-benzo[1,3]dioxole | Cl | 1.40-1.60 ppm: m + s: 13 H; 2.90 ppm: s: 4 H; 6.70 ppm: d: 1 H; 7.30 ppm: de: 1 H; 7.45 ppm-7.60 ppm: se: 4 H; 8.05 ppm: s: 1 H; 8.20 ppm: se: 1 H; 9.00 ppm: s: 1 H; 10.00 ppm: s: 1 H; 10.65 ppm: s: 1 H. |
| 37 | 5-methyl-spiro[benzo[1,3]dioxole-2,4'-piperidine] | Cl | LC/MS: MH⁺ = 594 |

TABLE 3-continued (I)

| Compounds | Ar₁ | X | NMR characterization |
|---|---|---|---|
| 38 | 5-methyl-benzo[1,3]dioxol-2-ylmethyl-N,N-bis(2-hydroxyethyl)amine substituent | Cl | 1.45 ppm: s: 9 H; 2.70 ppm: t: 4 H; 3.00 ppm: d: 2 H; 3.45 ppm: qd: 4 H; 4.35 ppm: t: 2 H; 6.20 ppm: t: 1 H; 6.75 ppm: d: 1 H; 7.25 ppm: d: 1 H; 7.50 ppm-7.70 ppm: m: 3 H; 7.90 ppm: se: 1 H; 8.05 ppm: s: 1 H; 8.10 ppm: se: 1 H; 9.05 ppm: s: 1 H; 10.10 ppm: s: 1 H; 10.70 ppm: s: 1 H. |
| 39 | 5-methyl-benzo[1,3]dioxol-2-ylmethyl-morpholine | Cl | 1.40 ppm: s: 9 H; 2.60 ppm: te: 4 H; 2.80 ppm: te: 2 H; 3.55 ppm: t: 4 H; 6.30 ppm: t: 1 H; 6.80 ppm: d: 1 H; 7.25 ppm: de: 1 H; 7.45 ppm-7.70 ppm: m: 3 H; 8.00 ppm: se: 1 H; 8.05 ppm: s: 1 H; 8.15 ppm: se: 1 H; 9.00 ppm: s: 1 H; 10.10 ppm: s: 1 H; 10.75 ppm: s: 1 H. |
| 40 | 5-methyl-benzo[1,3]dioxol-2-ylmethyl-N-tert-butylamine | Cl | 1.00 ppm: s: 9 H; 1.45 ppm: s: 9 H; 2.90 ppm: d: 2 H; 6.10 ppm: t: 1 H; 6.75 ppm: d: 1 H; 7.30 ppm: de: 1 H; 7.40 ppm-7.65 ppm: m: 3 H; 7.85 ppm: se: 1 H; 8.05 ppm: s: 1 H; 8.15 ppm: se: 1 H; 9.00 ppm: s: 1 H; 10.00 ppm: s: 1 H; 10.65 ppm: s: 1 H. |
| 41 | 5-methyl-benzo[1,3]dioxol-2-ylmethyl-N-Boc-piperazine | Cl | 1.35 ppm: s: 9 H; 1.45 ppm: s: 9 H; 2.45 ppm-2.60 ppm: mt: 4 H; 2.85: te: 2 H; 3.25-3.35 ppm: mt: 4 H; 6.30 ppm: t: 1 H; 6.80 ppm: d: 1 H; 7.25 ppm: de: 1 H; 7.45 ppm-7.70 ppm: m: 3 H; 8.05 ppm: s: 2 H; 8.15 ppm: se: 1 H; 9.05 ppm: s: 1 H; 10.10 ppm: s: 1 H; 10.70 ppm: s: 1 H. |
| 42 | 5-methyl-benzo[1,3]dioxol-2-ylmethyl-N-cyclopropylamine | Cl | 0.20 ppm: mt: 2 H; 0.35 ppm: mt: 2 H; 1.40 ppm: s: 9 H; 2.20 ppm: mt: 1 H; 2.35 ppm: se: 1 H; 2.95 ppm: d: 2 H; 6.20 ppm: t: 1 H; 6.75 ppm: d: 1 H; 7.25 ppm: de: 1 H; 7.45 ppm-7.60 ppm: m: 3 H; 7.85 ppm: se: 1 H; 8.05 ppm: s: 1 H; 8.10 ppm: se: 1 H; 9.00 ppm: s: 1 H; 10.00 ppm: s: 1 H; 10.65 ppm: s: 1 H. |

TABLE 3-continued (I)

| Compounds | Ar₁ | X | NMR characterization |
|---|---|---|---|
| 43 | (5-methyl-benzo[1,3]dioxol-2-yl)methyl-(cis-2,6-dimethylpiperidin-1-yl), Cis | Cl | 1.05 ppm: s: 3 H; 1.10 ppm: s: 3 H; 1.40 ppm: s: 9 H; 1.10-1.60 ppm: m: 6 H; 2.45-2.65 ppm: m: 2 H; 3.00 ppm: d: 2 H; 6.15 ppm: t: 1 H; 6.75 ppm: d: 1 H; 7.25 ppm: de: 1 H; 7.45 ppm-7.65 ppm: m: 3 H; 7.95 ppm: se: 1 H; 8.05 ppm: s: 1 H; 8.10 ppm: se: 1 H; 9.00 ppm: s: 1 H; 10.05 ppm: s: 1 H; 10.70 ppm: s: 1 H. |
| 44 | (5-methyl-benzo[1,3]dioxol-2-yl)methyl-piperazine | Cl | (DMSO + TFA) 1.30 ppm: s: 9 H; 3.40-3.90 ppm: m: 10 H; 6.75 ppm: t: 1 H; 6.95 ppm: d: 1 H; 7.25 ppm: de: 1 H; 7.55 ppm-7.75 ppm: m: 4 H; 8.55 ppm: se: 1 H; 9.20 ppm: s: 1 H. |
| 45 | (5-methyl-benzo[1,3]dioxol-2-yl)methyl-guanidine | Cl | (DMSO + TFA) 1.35 ppm: s: 9 H; 3.75 ppm: d: 2 H; 6.35 ppm: t: 1 H; 6.90 ppm: d: 1 H; 7.35 ppm: de: 1 H; 7.45 ppm-7.75 ppm: m: 4 H; 8.40 ppm: s: 1 H; 9.25 ppm: s: 1 H. |
| 46 | (5-methyl-benzo[1,3]dioxol-2-yl)methyl-acetamide | Cl | 1.40 ppm: s: 9 H; 1.80 ppm: s: 3 H; 3.50 ppm: de: 2 H; 6.15 ppm: t: 1 H; 6.80 ppm: d: 1 H; 7.35 ppm: de: 1 H; 7.45 ppm-7.65 ppm: m: 3 H; 7.85 ppm: se: 1 H; 8.00 ppm: s: 1 H; 8.10 ppm: se: 1 H; 8.20 ppm: t: 1 H; 9.00 ppm: s: 1 H; 10.00 ppm: s: 1 H; 10.70 ppm: s: 1 H. |
| 47 | (5-methyl-benzo[1,3]dioxol-2-yl)methyl-benzamide | Cl | 1.40 ppm: s: 9 H; 3.70 ppm: te: 2 H; 6.35 ppm: t: 1 H; 6.80 ppm: d: 1 H; 7.30 ppm: de: 1 H; 7.35 ppm-7.70 ppm: m: 6 H; 7.85 ppm: d: 2 H; 8.00 ppm: se: 1 H; 8.05 ppm: s: 1 H; 8.10 ppm: se: 1 H; 8.80 ppm: t: 1 H; 9.05 ppm: s: 1 H; 10.10 ppm: s: 1 H; 10.65 ppm: s: 1 H. |

TABLE 3-continued (I)

| Compounds | Ar₁ | X | NMR characterization |
|---|---|---|---|
| 48 | (6-methyl-1,3-benzodioxol-2-yl)methyl-NH-C(O)-cyclopropyl | Cl | 0.60-0.75 ppm: m: 4 H; 1.40 ppm: s: 9 H; 1.60 ppm: mt: 1 H; 3.55 ppm: mt: 2 H; 6.20 ppm: t: 1 H; 6.70 ppm: d: 1 H; 7.35 ppm: de: 1 H; 7.45 ppm-7.70 ppm: m: 3 H; 7.85 ppm: se: 1 H; 8.00 ppm: se: 1 H; 8.10 ppm: se: 1 H; 8.40 ppm: t: 1 H; 9.05 ppm: s: 1 H; 10.05 ppm: s: 1 H; 10.70 ppm: s: 1 H. |
| 49 | (6-methyl-1,3-benzodioxol-2-yl)methyl-NH-S(O)₂-CH₃ | Cl | 1.45 ppm: s: 9 H; 2.95 ppm: s: 3 H; 3.40 ppm: mt: 2 H; 6.25 ppm: t: 1 H; 6.80 ppm: d: 1 H; 7.40 ppm: de: 1 H; 7.45 ppm-7.65 ppm: m: 4 H; 7.85 ppm: se: 1 H; 8.05 ppm: s: 1 H; 8.15 ppm: se: 1 H; 9.00 ppm: s: 1 H; 10.10 ppm: s: 1 H; 10.60 ppm: s: 1 H. |
| 50 | (6-methyl-1,3-benzodioxol-2-yl)-C(O)-NH-tBu | Cl | 1.25 ppm: s: 9 H; 1.40 ppm: s: 9 H; 6.25 ppm: s: 1 H; 6.80 ppm: d: 1 H; 7.30 ppm: de: 1 H; 7.45 ppm-7.65 ppm: m: 3 H; 7.85 ppm: se: 1 H; 8.05 ppm: s: 1 H; 8.10 ppm: se: 2 H; 9.00 ppm: s: 1 H; 10.10 ppm: s: 1 H; 10.75 ppm: s: 1 H. |
| 51 | (6-methyl-1,3-benzodioxol-2-yl)-C(O)-NH-cyclopropyl | Cl | 0.40-0.70 ppm: mt: 4 H; 1.40 ppm: s: 9 H; 2.70 ppm: mt: 1 H; 6.30 ppm: s: 1 H; 6.80 ppm: d: 1 H; 7.40 ppm: de: 1 H; 7.45 ppm-7.65 ppm: m: 3 H; 7.85 ppm: se: 1 H; 8.05 ppm: s: 1 H; 8.15 ppm: se: 1 H; 8.60 ppm: d: 1 H; 9.05 ppm: s: 1 H; 10.10 ppm: s: 1 H; 10.65 ppm: s: 1 H. |
| 52 | (6-methyl-1,3-benzodioxol-2-yl)-C(O)-pyrrolidin-1-yl | Cl | 1.40 ppm: s: 9 H; 1.70-1.95 ppm: m: 4 H; 3.35 ppm: t: 2 H; 3.60 ppm: t: 2 H; 6.75 ppm: s: 1 H; 6.85 ppm: d: 1 H; 7.30 ppm: de: 1 H; 7.45 ppm-7.65 ppm: m: 3 H; 8.00 ppm: se: 1 H; 8.05 ppm: s: 1 H; 8.15 ppm: se: 1 H; 9.05 ppm: s: 1 H; 10.10 ppm: s: 1 H; 10.65 ppm: s: 1 H. |

TABLE 3-continued (I)

| Compounds | Ar₁ | X | NMR characterization |
|---|---|---|---|
| 53 | (5-methyl-benzo[1,3]dioxole-2-carboxylic acid N-isopropyl-N-methyl-amide) | Cl | 1.05 ppm: d: 3 H; 1.20 ppm: d: 3 H; 1.40 ppm: s: 9 H; 2.70 ppm and 2.90 ppm: 2 s: 3 H; 4.20-4.60 ppm: m: 1 H; 6.80-7.05 ppm: mt: 2 H; 7.30 ppm: de: 1 H; 7.45 ppm-7.65 ppm: m: 3 H; 8.00 ppm: se: 1 H; 8.05 ppm: s: 1 H; 8.15 ppm: se: 1 H; 9.05 ppm: s: 1 H; 10.15 ppm: s: 1 H; 10.60 ppm: s: 1 H. |
| 54 | (5-methyl-benzo[1,3]dioxole-2-carboxylic acid methylamide) | Cl | 1.40 ppm: s: 9 H; 2.65 ppm: d: 3 H; 6.35 ppm: s: 1 H; 6.85 ppm: d: 1 H; 7.40 ppm: de: 1 H; 7.45 ppm-7.65 ppm: m: 3 H; 7.85 ppm: se: 1 H; 8.00 ppm: s: 1 H; 8.15 ppm: se: 1 H; 8.50 ppm: qd: 1 H; 9.05 ppm: s: 1 H; 10.10 ppm: s: 1 H; 10.60 ppm: s: 1 H. |
| 55 | (tert-butyl carbamate of 2-methyl-2-(2-aminoethyl)-5-methyl-benzo[1,3]dioxole) | Cl | 1.35 ppm: s: 9 H; 1.40 ppm: s: 9 H; 1.60 ppm: s: 3 H; 2.65 ppm: t: 2 H; 3.00-3.20 ppm: mt: 2 H; 6.70 ppm: d: 1 H; 6.80 ppm: t: 1 H; 7.20 ppm: de: 1 H; 7.45 ppm-7.70 ppm: m: 3 H; 7.80 ppm: se: 1 H; 8.05 ppm: s: 2 H; 9.00 ppm: s: 1 H; 10.00 ppm: s: 1 H; 10.60 ppm: s: 1 H. |
| 56 | (2-(2-aminoethyl)-2-methyl-5-methyl-benzo[1,3]dioxole) | Cl | 1.40 ppm: s: 9 H; 1.60 ppm: s: 3 H; 2.00 ppm: t: 2 H; 2.70 ppm: t: 2 H; 6.70 ppm: d: 1 H; 7.20 ppm: de: 1 H; 7.50 ppm-7.70 ppm: m: 4 H; 7.80 ppm: se: 1 H; 8.05 ppm: s: 1 H; 9.00 ppm: s: 1 H; 10.00 ppm: s: 1 H; 10.70 ppm: s: 1 H. |
| 57 | (tert-butyl carbamate of 2-(2-aminoethyl)-5-methyl-benzo[1,3]dioxole) | Cl | 1.35 ppm: s: 9 H; 1.45 ppm: s: 9 H; 2.00 ppm: qd: 2 H; 3.10: qd: 2 H; 6.20 ppm: t: 1 H; 6.75 ppm: d: 1 H; 6.95 ppm: t: 1 H; 7.30 ppm: de: 1 H; 7.45 ppm-7.65 ppm: m: 3 H; 7.90 ppm: se: 1 H; 8.05 ppm: s: 1 H; 8.10 ppm: se: 1 H; 9.05 ppm: s: 1 H; 10.10 ppm: s: 1 H; 10.65 ppm: s: 1 H. |
| 58 | (2-(2-aminoethyl)-5-methyl-benzo[1,3]dioxole) | Cl | (DMSO + TFA) 1.25 ppm: s: 9 H; 2.20 ppm: qd: 2 H; 3.00 ppm: t: 2 H; 6.30 ppm: t: 1 H; 6.75 ppm: d: 1 H; 7.25 ppm: de: 1 H; 7.50 ppm-7.70 ppm: m: 4 H; 8.50 ppm: s: 1 H; 9.15 ppm: s: 1 H. |

TABLE 3-continued (I)

| Compounds | Ar₁ | X | NMR characterization |
|---|---|---|---|
| 59 | benzodioxine-CH₂OH (6-methyl) | Cl | 1.45 ppm: s: 9 H; 3.50-4.35 ppm: m: 5 H; 5.05 ppm: t: 1 H; 6.75 ppm: d: 1 H; 7.30 ppm: de: 1 H; 7.45 ppm-7.70 ppm: m: 3 H; 7.90 ppm: se: 1 H; 8.05 ppm: s: 1 H; 8.10 ppm: se: 1 H; 9.00 ppm: s: 1 H; 10.00 ppm: s: 1 H; 10.60 ppm: s: 1 H. |
| 60 | benzodioxine-CH₂NH₂ (6-methyl) | Cl | 1.40 ppm: s: 9 H; 2.70-2.85 ppm: m: 2 H; 3.90-4.05 ppm: m: 2 H; 4.35 ppm: d: 1 H; 6.75 ppm: d: 1 H; 7.35 ppm: de: 1 H; 7.45 ppm-7.70 ppm: m: 4 H; 7.85 ppm: se: 1 H; 8.05 ppm: s: 1 H; 9.00 ppm: s: 1 H; 10.00 ppm: s: 1 H; 10.60 ppm: s: 1 H. |
| 61 | 5-methyl-2,3-dihydrobenzofuran | Cl | 1.40 ppm: s: 9 H; 3.15 ppm: t: 2 H; 4.50 ppm: t: 2 H; 6.65 ppm: d: 1 H; 7.45 ppm-7.65 ppm: m: 4 H; 8.00 ppm: s: 1 H; 8.05 ppm: se: 1 H; 8.30 ppm: se: 1 H; 9.00 ppm: s: 1 H; 10.00 ppm: s: 1 H; 10.70 ppm: s: 1 H. |
| 62 | 6-methyl-2,3-dihydrobenzofuran | Cl | 1.40 ppm: s: 9 H; 3.10 ppm: t: 2 H; 4.50 ppm: t: 2 H; 7.10 ppm: d: 1 H; 7.35 ppm: dd: 1 H; 7.45 ppm-7.70 ppm: m: 3 H; 7.75 ppm: s: 1 H; 8.05 ppm: s: 1 H; 8.15 ppm: s: 1 H; 9.05 ppm: s: 1 H; 10.10 ppm: s: 1 H; 10.65 ppm: s: 1 H. |
| 63 | benzodioxole-CH₂NH₂ (methyl) | Cl | 1.35 ppm: s: 9 H; 1.40-1.75 ppm: m: 2 H; 2.90 ppm: d: 2 H; 6.15 ppm: t: 1 H; 6.60 ppm-6.80 ppm: mt: 2 H; 7.40 ppm-7.65 ppm: mt: 4 H; 8.05 ppm: s: 2 H; 9.05 ppm: s: 1 H; 9.35 ppm: s: 1 H; 10.45 ppm: s: 1 H. |
| 64 | benzodioxole-CH₂-(3-fluoropyrrolidinyl) (methyl) | Cl | 1.40 ppm: s: 9 H; 2.10-2.35 ppm: mt: 2 H; 2.80 ppm-3.15 ppm: m: 6 H; 6.30 ppm: t: 1 H; 6.80 ppm: d: 1 H; 7.25 ppm: de: 1 H; 7.45 ppm-7.70 ppm: m: 3 H; 8.05 ppm: s: 2 H; 8.15 ppm: s: 1 H; 9.05 ppm: s: 1 H; 10.10 ppm: s: 1 H; 10.60 ppm: s: 1 H. |

TABLE 3-continued (I)

| Compounds | Ar₁ | X | NMR characterization |
|---|---|---|---|
| 65 | 5-methyl-benzo[1,3]dioxole-2-carbonyl-morpholine | Cl | 1.40 ppm: s: 9 H; 3.40-3.70 ppm: m: 8 H; 6.85 ppm: d: 1 H; 7.00 ppm: s: 1 H; 7.30 ppm: dd: 1 H; 7.45 ppm-7.70 ppm: m: 3 H; 8.05 ppm: s: 2 H; 8.15 ppm: s: 1 H; 9.05 ppm: s: 1 H; 10.10 ppm: s: 1 H; 10.65 ppm: s: 1 H. |
| 66 | 2-(pyrrolidin-1-ylmethyl)-5-methyl-benzo[1,3]dioxole | Cl | 1.40 ppm: s: 9 H; 1.60-1.75 ppm: m: 4 H; 2.50 ppm-2.65 ppm: m: 4 H; 2.75 ppm-3.00 ppm: mt: 2 H; 6.25 ppm: t: 1 H; 6.75 ppm: d: 1 H; 7.25 ppm: de: 1 H; 7.45 ppm-7.70 ppm: m: 3 H; 7.95 ppm: s: 1 H; 8.05 ppm: s: 1 H; 8.15 ppm: s: 1 H; 9.05 ppm: s: 1 H; 10.10 ppm: s: 1 H; 10.70 ppm: s: 1 H. |
| 67 | 2-(aminomethyl)-5-methyl-benzo[1,3]dioxole | Br | 1.40 ppm: s: 9 H; 1.60 ppm: se: 2 H; 2.90 ppm: d: 2 H; 6.10 ppm: t: 1 H; 6.75 ppm: d: 1 H; 7.20 ppm-7.40 ppm: m: 2 H; 7.70 ppm-7.85 ppm: d: 4 H; 8.00 ppm: s: 1 H; 9.05 ppm: s: 1 H; 10.05 ppm: s: 1 H; 10.70 ppm: s: 1 H. |
| 68 | 2-{[(trans-4-aminocyclohexyl)amino]methyl}-5-methyl-benzo[1,3]dioxole (trans) | Cl | 0.95 ppm: t: 4 H; 1.35 ppm: s: 9 H; 1.60-1.80 ppm: m: 4 H; 2.25 ppm-2.45 ppm: m: 2 H; 2.85 ppm: d: 2 H; 6.10 ppm: t: 1 H; 6.70 ppm: d: 1 H; 7.25 ppm: d: 1 H; 7.40 ppm-7.60 ppm: m: 3 H; 7.85 ppm: se: 1 H; 8.00 ppm: s: 1 H; 9.00 ppm: s: 1 H; 10.00 ppm: s: 1 H; 10.65 ppm: s: 1 H. |
| 80 | N-methyl-7-methyl-2,3-dihydro-benzo[1,4]dioxine-2-carboxamide | Cl | 1.40 ppm: s: 9 H; 2.65 ppm: d: 3 H; 4.10-4.35 ppm: mt: 2 H; 4.65-4.75 ppm: mt: 1 H; 6.80 ppm: d: 1 H; 7.35 ppm: dd: 1 H; 7.45 ppm-7.70 ppm: mt: 3 H; 8.00-8.15 ppm: m: 4 H; 9.05 ppm: s: 1 H; 10.10 ppm: s: 1 H; 10.60 ppm: s: 1 H. |

TABLE 3-continued (I)

| Compounds | Ar₁ | X | NMR characterization |
|---|---|---|---|
| 81 | (6-methyl-benzo[1,3]dioxol-2-yl)methyl-NH-CH₂-cyclopropyl | Cl | 0.00-0.10 ppm: m: 2 H; 0.30-0.40 ppm: m: 2 H; 0.80-0.90 ppm: m: 1 H; 1.40 ppm: s: 9 H; 1.85 ppm: se: 1 H; 2.40-2.50 ppm: m: 2 H; 2.95 ppm: d: 2 H; 6.20 ppm: t: 1 H; 6.75 ppm: d: 1 H; 7.25 ppm: de: 1 H; 7.45-7.70 ppm: m: 3 H; 7.90 ppm: s: 1 H; 8.05 ppm: s: 1 H; 8.20 ppm: s: 1 H; 9.00 ppm: s: 1 H; 10.05 ppm: s: 1 H; 10.70 ppm: s: 1 H. |

TABLE 4

| Compounds | Structure | NMR characterization |
|---|---|---|
| 69 | (structure) | 1.30 ppm: s: 9H; 3.90 d: 2H; 5.00 ppm: d: 4H; 7.25 ppm: d: 1H; 7.40 ppm-7.65 ppm: m: 4H; 7.90 ppm: d: 1H; 8.00 ppm: s: 1H; 8.10 ppm: s: 1H; 8.50 ppm: s: 1H; 9.10 ppm: s: 1H; 10.10 ppm: s: 1H; 10.25 ppm: s: 1H. |
| 70 | (structure) | 1.00 ppm: mt: 3H; 3.10 ppm: qt: 2H; 3.90 d: 2H; 5.00 ppm: d: 4H; 7.25 ppm: d: 1H; 7.40 ppm-7.65 ppm: m: 3H; 7.75 ppm: d: 1H; 8.05 ppm: s: 1H; 8.10 ppm: s: 1H; 8.25 ppm: s: 1H; 8.60 ppm: s: 1H; 9.10 ppm: s: 1H; 10.20 ppm: s: 1H; 10.30 ppm: s: 1H. |
| 71 | (structure) | 1.65 ppm: s: 9H; 5.00 ppm: s: 4H; 7.20 ppm: d: 1H; 7.50 ppm-7.70 ppm: m: 5H; 8.25 ppm: s: 1H; 8.30 ppm: s: 1H; 9.20 ppm: s: 1H; 10.40 ppm: s: 1H; 12.80 ppm: s: 1H. |

TABLE 4-continued

| Compounds | Structure | NMR characterization |
|---|---|---|
| 72 | 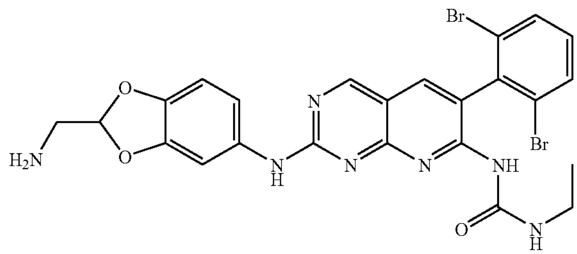 | (DMSO + TFA) 1.10 ppm: t: 3H; 3.20 ppm: qd: 2H; 3.45 ppm: d: 2H; 6.45 ppm: t: 1H; 7.00 ppm: d: 1H; 7.25 ppm: de: 1H; 7.45 ppm: t: 1H; 7.70 ppm: se: 1H; 7.85 ppm: s: 1H; 7.90 ppm: s: 1H; 8.50 ppm: s: 1H; 9.20 ppm: s: 1H. |
| 73 | 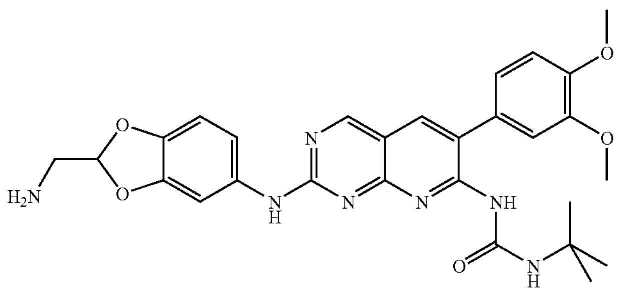 | 1.40 ppm: s: 9H; 1.60-1.80 ppm: se: 2H; 2.95 ppm: d: 2H; 3.80 ppm: s: 3H; 3.85 ppm: s: 3H; 6.10 ppm: t: 1H; 6.75 ppm: d: 1H; 6.95 ppm-7.35 ppm: m: 5H; 7.80 ppm: s: 1H; 8.05 ppm: s: 1H; 9.05 ppm: s: 1H; 9.95 ppm: s: 1H; 10.55 ppm: s: 1H. |
| 74 | 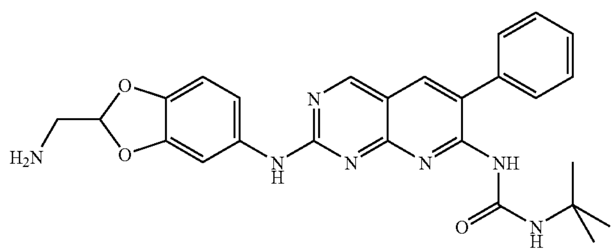 | 1.40 ppm: s: 9H; 1.50-1.70 ppm: se: 2H; 2.90 ppm: d: 2H; 6.10 ppm: t: 1H; 6.75 ppm: d: 1H; 7.10 ppm: se: 1H; 7.30 ppm: d: 1H; 7.50 ppm: se: 5H; 7.85 ppm: s: 1H; 8.10 ppm: s: 1H; 9.05 ppm: s: 1H; 9.95 ppm: s: 1H; 10.50 ppm: s: 1H. |
| 75 | 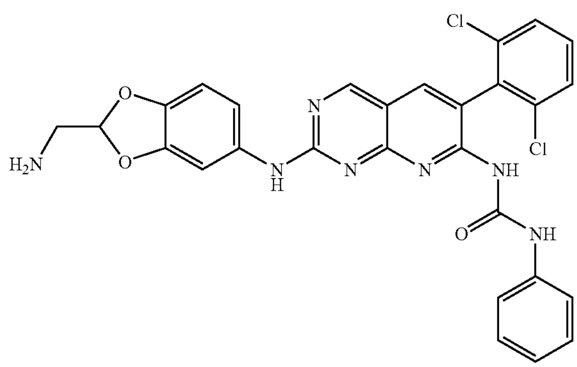 | 1.30 ppm-1.80 ppm: se: 2H; 3.00 ppm: d: 2H; 6.20 ppm: t: 1H; 6.85 ppm: d: 1H; 7.10 ppm: t: 1H; 7.20 ppm: d: 1H; 7.40 ppm: t: 2H; 7.45 ppm 7.70 ppm: m: 6H; 8.10 ppm: s: 2H; 9.10 ppm: s: 1H; 10.15 ppm: s: 1H; 13.20 ppm: s: 1H. |
| 76 | 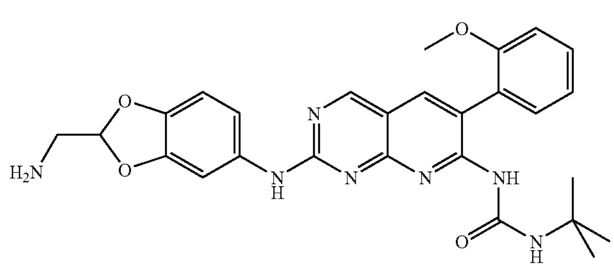 | 1.40 ppm: s: 9H; 1.50-1.65 ppm: se: 2H; 2.90 ppm: d: 2H; 3.80 ppm: s: 3H; 6.10 ppm: t: 1H; 6.75 ppm: d: 2H; 7.10 ppm-7.40 ppm: m: 4H; 7.50 ppm: t: 1H; 7.85 ppm: s: 1H; 8.00 ppm: s: 1H; 9.05 ppm: s: 1H; 10.00 ppm: s: 1H; 10.50 ppm: s: 1H. |

TABLE 4-continued

| Compounds | Structure | NMR characterization |
|---|---|---|
| 77 | 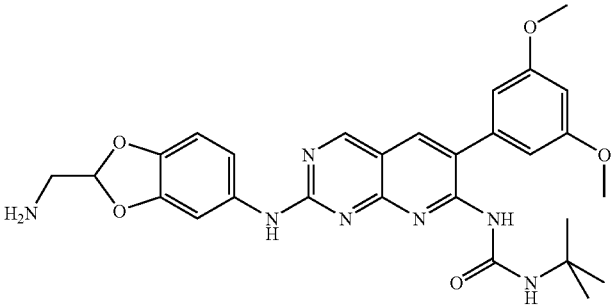 | 1.40 ppm: s: 9H; 1.50-1.65 ppm: s: 2H; 2.90 ppm: d: 2H; 3.80 ppm: s: 6H; 6.10 ppm: t: 1H; 6.60 ppm: s: 3H; 6.75 ppm: d: 1H; 7.20 ppm-7.35 ppm: mt: 2H; 7.80 ppm: s: 1H; 8.10 ppm: s: 1H; 9.05 ppm: s: 1H; 10.00 ppm: s: 1H; 10.50 ppm: s: 1H. |
| 78 | 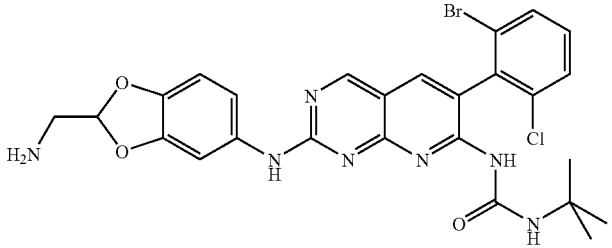 | 1.35 ppm: s: 9H; 1.50-1.70 ppm: se: 2H; 2.85 ppm: d: 2H; 6.05 ppm: t: 1H; 6.70 ppm: d: 1H; 7.20 ppm-7.80 ppm: mt: 5H; 7.95 ppm: se: 1H; 8.00 ppm: s: 1H; 9.00 ppm: s: 1H; 10.00 ppm: s: 1H; 10.60 ppm: s: 1H. |
| 79 | 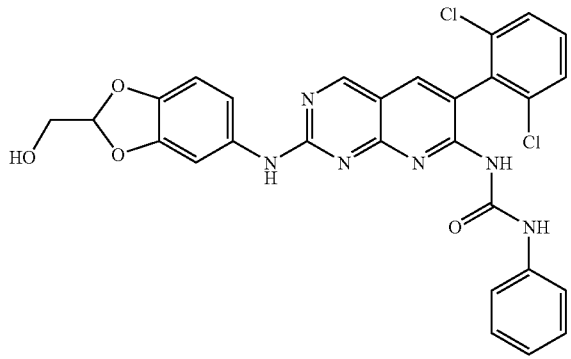 | LC/MS: MH$^+$ = 575 |
| 82 | 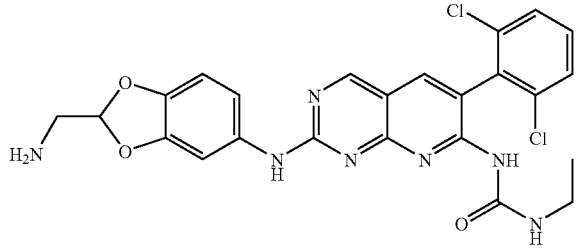 | (DMSO + TFA) 1.05 ppm: t: 3H; 3.20 ppm: qd: 2H; 3.40 ppm: d: 2H; 6.45 ppm: t: 1H; 6.95 ppm: d: 1H; 7.20 ppm: de: 1H; 7.50-7.75 ppm: m: 4H; 8.55 ppm: s: 1H; 9.20 ppm: s: 1H. |
| 83 | 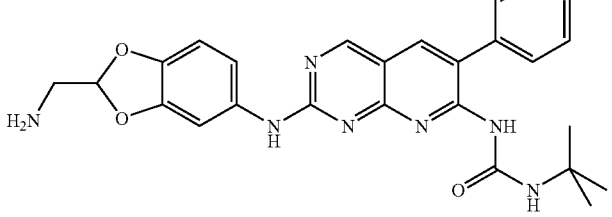 | 1.40 ppm: s: 9H; 1.60 ppm: se: 2H; 2.90 ppm: d: 2H; 6.05 ppm: t: 1H; 6.75 ppm: d: 1H; 7.30 ppm: d: 1H; 7.45 ppm-7.60 ppm: mt: 2H; 7.75-7.90 ppm: mt: 3H; 8.00 ppm: s: 1H; 9.00 ppm: s: 1H; 10.05 ppm: s: 1H; 10.60 ppm: s: 1H. |

Compound 34 was separated into its two enantiomers by chiral chromatography. Dextrogyratory enantiomer: $[\alpha]_D=+72.1°$; t=25° C.; C=0.5 (MeOH). Laevogyratory enantiomer: $[\alpha]_D=-73.0°$; t=25° C.; C=0.5 (MeOH).

Databases of products according to the invention were also prepared by employing conventional techniques of combinatorial chemistry and applying the preparation procedures described in the present invention. The structures of the products prepared and their characterization are presented here.

The LC/MS analyses were carried out on a Micromass model LCT device, coupled to an HP1100 model device. The extent of the compounds was measured with a G1315A diode array detector in the wavelength region from 200 to 600 nm and using a Sedex model 65 light scattering evaporative detector (LSED). The mass spectra were recorded in the range from 180 to 800 (m/z). The data were analyzed using Micromass MassLynx software. The separations were performed on a Hypersil BDS C18 column (50×4.6 mm), particle size 3 μm. Elution with a gradient from 5 to 90% of acetonitrile comprising 0.05% (v/v) of trifluoroacetic acid (TFA) in water comprising 0.05% (v/v) of TFA over 3.5 minutes at a flow rate of 1 ml/minute. The total duration of the procedure, including the reequilibrating of the column, is 7 minutes.

TABLE 5

| Compounds | $R_1$ | $Ar_2$ | LC/MS (retention time (minutes): $MH^+$; $MH^-$) |
|---|---|---|---|
| 1 | Phenyl | 2,6-Dichlorophenyl | 4.42; 616; 614 |
| 2 | t-Butyl | 3,5-Dimethoxyphenyl | 4.24; 588; 586 |
| 3 | Ethyl | 2,6Dichlorophenyl | 3.77; 568; 566 |
| 4 | t-Butyl | 3,4-Dimethoxyphenyl | 3.93; 588; 586 |
| 5 | tButyl | Phenyl | 3.80; 528; 526 |
| 6 | t-Butyl | 2-Methoxyphenyl | 4.06; 558; 556 |
| 7 | t-Butyl | 2,6-Dibromophenyl | 4.32; 685; 684 |
| 8 | t-Butyl | 2-Bromo-6-chlorophenyl | 4.29; 640; 638 |
| 9 | Ethyl | 2,6-Dibromophenyl | 3.83; 658; 656 |
| 10 | Phenyl | 2-Bromo-6-chlorophenyl | 4.46; 660; 658 |
| 11 | Phenyl | 2,6-Dibromophenyl | 4.49; —; 704 |

TABLE 6

| Compounds | $R_1$ | $Ar_2$ | LC/MS (retention time (minutes): $MH^+$) |
|---|---|---|---|
| 1 | Phenyl | 2,6-Dichlorophenyl | 4.75; 543.28 |
| 2 | t-Butyl | 3,5-Dimethoxyphenyl | 4.52; 515.42 |
| 3 | Ethyl | 2,6-Dichlorophenyl | 4.95; 495.30 |
| 4 | t-Butyl | 3,4-Dimethoxyphenyl | 4.21; 515.43 |
| 5 | tButyl | Phenyl | 4.42; 455.41 |

TABLE 6-continued

| Compounds | $R_1$ | $Ar_2$ | LC/MS (retention time (minutes): $MH^+$) |
|---|---|---|---|
| 6 | t-Butyl | 2-Methoxyphenyl | 4.34; 485.41 |
| 7 | t-Butyl | 2,6-Dibromophenyl | 4.63; 611.25 |
| 8 | t-Butyl | 2-Bromo-6-chlorophenyl | 4.72; 567.09 |
| 9 | Ethyl | 2,6-Dibromophenyl | 4.14; 582.96 |
| 10 | Phenyl | 2-Bromo-6-chlorophenyl | 4.88; 587.06 |
| 11 | Phenyl | 2,6-Dibromophenyl | 4.91; 630.97 |

The compounds of the invention underwent pharmacological tests in order to determine their anti-cancer activity.

The compounds of formula (I) of the present invention were tested in vitro on a panel of tumour lines of human origin deriving from the following:

breast cancer: MDA-MB231 (American Type Culture Collection, Rockville, Md., USA, ATCC-HTB26), MDA-A1 or MDA-ADR (known as the multi-drug resistant line, MDR, and described by E. Collomb et al., in Cytometry, 12(1):15-25, 1991), and MCF7 (ATCC-HTB22), prostate cancer: DU145 (ATCC-HTB81) and PC3 (ATCC-CRL1435), colon cancer: HCT116 (ATCC-CCL247) and HCT15 (ATCC-CCL225), lung cancer: H460 (described by Carmichael in Cancer Research 47 (4):936-942, 1987 and filed by the National Cancer Institute, Frederick Cancer Research and Development Center, Frederick, Md., USA), glioblastoma (SF268 described by Westphal in Biochemical & Biophysical Research Communications 132 (1): 284-289, 1985 and filed by the National Cancer Institute, Frederick Cancer Research and Development Center, Frederick, Md., USA), leukaemia (CMLT1 described by Kuriyama et al. in Blood, 74: 1989, 1381-1387, by Soda et al. in the British Journal of Haematology, 59: 1985, 671-679 and by Drexler, in Leukemia Research, 18: 1994, 919-927 and filed by DSMZ, Mascheroder Weg 1b, 38124 Brunswick, Germany).

Proliferation and cellular viability were determined by means of a test using 3-(4,5-dimethylthiazol-2-yl)-5-(3-carboxymethoxyphenyl)-2-(4-sulphophenyl)-2H-tetrazolium (MTS) in accordance with Fujishita T. et al., Oncology, 2003, 64 (4), 399-406. In this test, the mitochondrial capacity of living cells to transform MTS into a coloured compound after incubating a compound of formula (I) in accordance with the invention for 72 hours is measured. The concentrations of the compound of the invention which result in a 50% drop in proliferation and cellular viability ($CI_{50}$) were in the range 1 nM to 10 μM depending on the tumour line and the test compound.

Thus, in accordance with the present invention, it appears that compounds of formula (I) cause a drop in proliferation and viability of tumour cells. It thus appears that the compounds of the invention have an anti-cancer activity and an activity in the treatment of other proliferative diseases such as psoriasis, restenosis, arteriosclerosis, AIDS, for example, and in diseases caused by the proliferation of cells of the smooth vascular muscle cells and in rheumatoid polyarthritis.

Thus, in accordance with a further aspect, the invention concerns medicaments which comprise a compound of formula (I) or an addition salt of the latter with a pharmaceutically acceptable acid or a hydrate or a solvate of the compound of formula (I).

Said medicaments are of use in therapy, in particular in the treatment or prevention of diseases caused or exacerbated by the proliferation of cells, in particular tumour cells.

As an inhibitor of tumour cell proliferation, said compounds may be used in the prevention and treatment of leukaemias, both primary and metastatic solid tumours, carcinomas and cancers, in particular: breast cancer; lung cancer; cancer of the small intestine; cancer of the colon and rectum; cancer of the respiratory tracts, of the oropharynx and the hypopharynx; cancer of the oesophagus; cancer of the liver, stomach cancer, cancer of the biliary canals, cancer of the biliary vesicle, cancer of the pancreas; cancers of the urinary tracts including the kidney, urothelium and bladder; cancers of the female genital tract including cancer of the uterus, the neck of the uterus, the ovaries, chloriocarcinoma and trophoblastoma; cancers of the male genital tract including cancer of the prostate, of the seminal vesicles, the testicles, germinal cell tumours; cancers of the endocrinal glands including cancer of the thyroid, the pituitary, of the adrenal glands; skin cancers, including haemangiomas, melanomas, sarcomas, including Kaposi's sarcoma; tumours of the brain, nerves, eyes, meninges, including astrocytomas, gliomas, glioblastomas, retinoblastomas, neurinomas, neuroblastomas, schwannomas, meningiomas, malignant haematopoietic tumours; leukaemias (Acute Lymphocytic Leukemia (ALL), Acute Myeloid Leukemia (AML), Chronic Myeloid Leukemia (CML), Chronic lymphocytic leukemia (CLL)), chloromas, plasmocytomas, T or B cell leukaemias, non Hodgkins or Hodgkins lymphomas, myelomas, and various malignant haemopathies.

In a further aspect, the present invention concerns pharmaceutical compositions comprising a compound of the invention as an active principle. Said pharmaceutical compositions contain an effective dose of at least one compound in accordance with the invention or a pharmaceutically acceptable salt, a hydrate or a solvate of said compound, and at least one pharmaceutically acceptable excipient.

The choice of said excipients is dependent on the pharmaceutical form and the desired mode of administration; they are selected from the usual excipients, which are known to the skilled person.

In pharmaceutical compositions of the present invention for oral, sublingual, subcutaneous, intramuscular, intravenous, topical, local, intratracheal, intranasal, transdermal or rectal administration, the active principle of formula (I) above, or possibly its optional salt, solvate or hydrate, may be administered in a unitary administration form, mixed with conventional pharmaceutical excipients, to animals or to human beings for prophylactic treatment or for the treatment of the diseases or disorders cited above.

Appropriate unitary forms of administration comprise forms for oral administration such as tablets, soft or hard gelules, powders, granules and oral solutions or suspensions, sublingual, buccal, intratracheal, intraocular, intranasal forms of administration, forms for inhalation, forms for topical, transdermal, subcutaneous, intramuscular or intravenous administration, forms for rectal administration and implants. For topical administration, the compounds of the invention may be used in creams, gels, pomades or lotions.

An example of a unitary form of administration for a compound of the invention in the form of a tablet may comprise the following components:

| | |
|---|---:|
| Compound of the invention | 50.0 mg |
| Mannitol | 223.75 mg |
| Croscarmellose, sodium form | 6.0 mg |
| Corn starch | 15.0 mg |
| Hydroxypropylmethyl cellulose | 2.25 mg |
| Magnesium stearate | 3.0 mg |

The above compounds of formula (I) may be used in daily doses of 0.002 to 2000 mg per kilogram of body weight of the mammal to be treated, preferably in daily doses of 0.1 mg to 300 mg/kg. In humans, the dose may preferably be from 0.02 to 10000 mg per day, more particularly 1 to 3000 mg depending on the age of the subject to be treated and the type of treatment: prophylactic or curative.

Particular cases may arise for which higher or lower doses are appropriate; such doses also fall within the scope of the invention. The usual practice is for the physician to determine the dosage appropriate for each patient depending on the mode of administration and the patient's weight and response.

In a further aspect, the present invention also concerns a method for treating the diseases indicated above which comprises administering to a patient an effective dose of a compound of the invention or one of its pharmaceutically acceptably salts, hydrates or solvates.

In accordance with the present invention, the compound or compounds of formula (I) may be administered in association with one or more anticancerous active principles, in particular antitumour compounds such as alkylating agents, for example alkylsulphonates (busulfan), dacarbazine, procarbazine, nitrogen mustards (chlormethine, melphalan, chlorambucil), cyclophosphamide, ifosfamide; nitrosoureas such as carmustine, lomustine, semustine, streptozocine; antineoplasic alkaloids such as vincristine, vinblastine; taxanes such as paclitaxel or taxotere; antineoplasic antibiotics such as actinomycin; intercalating agents, antineoplasic antimetabolites, folate antagonists, methotrexate; purine synthesis inhibitors; purine analogues such as mercaptopurine, 6-thioguanine; pyrimidine synthesis inhibitors, aromatase inhibitors, capecitabine, pyrimidine analogues such as fluorouracil, gemcitabine, cytarabine and cytosine arabinoside; brequinar; topoisomerase inhibitors such as camptothecine or etoposide; anticancer hormonal agonists and antagonists such as tamoxifen; kinase inhibitors, imatinib; growth factor inhibitors; antiinflammatories such as pentosane polysulphate, corticosteroids, prednisone, dexamethasone; antitopoisomerases such as etoposide, antracyclins including doxorubicin, bleomycin, mitomycin and methramycin; anticancerous metallic complexes, platinum complexes, cisplatinum, carboplatinum, oxaliplatinum; alpha interferon, triphenylthiophosphoramide, altretamine; antiangiogenic agents; thalidomide; immunotherapeutic adjuvants; vaccines.

According to the present invention, the compounds of the formula (I) may also be administered in association with one or more other active principles used in one of the diseases indicated above, for example an anti-emitic agent, a pain killer, an anti-inflammatory, an anti-cachexy agent.

A product of the invention may be used to manufacture a drug for use in treating a pathological condition, in particular cancer.

The present invention also concerns therapeutic compositions containing a compound of the invention, in association with a pharmaceutically acceptable excipient which depends on the selected mode of administration. The pharmaceutical composition may be in the form of a solid, liquid or liposomes.

Examples of solid compositions which may be cited are powders, capsules and tablets. The oral forms also include solid forms protected from the acidic medium of the stomach. The supports used for the solid forms are constituted in particular by mineral supports such as phosphates or carbonates, or organic supports such as lactose, celluloses, starch or polymers. The liquid forms are constituted by solutions, suspensions or dispersions. They contain, as the dispersant, either water or an organic solvent (ethanol, NMP or others) or mixtures of surfactants and solvents or complexing agents and solvents.

The liquid forms are preferably injectable and for this reason will have a formulation suitable for such a use.

Acceptable injection modes include intravenous, intraperitoneal, intramuscular and sub-cutaneous; the intravenous route is preferred.

The dose of the compounds of the invention which is administered will be adapted by the physician as a function of the method of administration to the patient and the condition of the patient.

The compounds of the present invention may be administered alone or as a mixture with other anticancer agents. Possible combinations which may be cited are as follows:

alkylating agents, in particular cyclophosphamide, melphalan, ifosfamide, chlorambucil, busulfan, thiotepa, prednimustine, carmustine, lomustine, semustine, steptozotocin, decarbazine, temozolomide, procarbazine and hexamethylmelamine;

platinum derivatives such as cisplatinum, carboplatinum or oxaliplatinum;

antibiotic agents, in particular bleomycin, mitomycin and dactinomycin;

antimicrotubule agents, in particular vinblastine, vincristine, vindesine, vinorelbine or taxoids (paclitaxel and docetaxel);

antracyclins such as doxorubicin, daunorubicin, idarubicin, epirubicin, mitoxantrone or losoxantrone;

group I and II topoisomerases such as etoposide, teniposide, amsacrine, irinotecan, topotecan and tomudex;

fluoropyrimidines such as 5-fluorouracile, UFT or floxuridine;

cytidine analogues such as 5-azacytidine, cytarabine, gemcitabine, 6-mercaptomurine, 6-thioguanine;

adenosine analogues such as pentostatin, cytarabine or fludarabine phosphate;

methotrexate and folinic acid;

various enzymes and compounds, such as L-asparaginase, hydroxyurea, trans-retinoic acid, suramine, dexrazoxane, amifostine, herceptin and oestrogenic or androgenic hormones;

antivasculaires agents, such as combretastatin or colchicine derivatives and their prodrugs.

It is also possible to combine the compounds of the present invention with radiation treatment. Said treatments may be administered simultaneously, separately or sequentially. The treatment will be adapted by the physician to the patient to be treated.

What is claimed is:

1. A compound of formula (II):

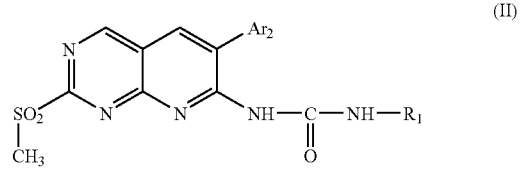

wherein:

$R_1$ is selected from the group consisting of $(C_1$-$C_6)$alkyl, $(C_3$-$C_7)$cycloalkyl, $CH_2COR_4$, phenyl and phenyl substituted with one or more substituents independently selected from hydroxy, halogen, or $(C_1$-$C_6)$alkyl; and $Ar_2$ represents a phenyl group which is unsubstituted or substituted 1 to 5 times with substituents independently selected from a halogen atom or a $(C_1$-$C_4)$alkyl, trifluoromethyl or $(C_1$-$C_4)$alkoxy group.

2. The compound according to claim 1 wherein $Ar_2$ is selected from the group consisting of phenyl, 2-methoxyphenyl, 2,6-dichlorophenyl, 3,5-dimethoxyphenyl, 3,4-dimethoxyphenyl, 2,6-dibromophenyl, 2-bromo-6-chlorophenyl, 2,4-dichlorophenyl and 3,5-dichlorophenyl.

3. The compound according to claim 1 wherein $R_1$ is selected from ethyl, tert-butyl and phenyl.

4. A compound of the formula:

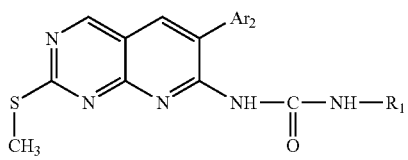

wherein:

$R_1$ is selected from the group consisting of $(C_1$-$C_6)$alkyl, $(C_3$-$C_7)$cycloalkyl, $CH_2COR_4$, phenyl and phenyl substituted with one or more substituents independently selected from hydroxy, halogen, or $(C_1$-$C_6)$alkyl; and $Ar_2$ represents a phenyl group which is unsubstituted or substituted 1 to 5 times with substituents independently selected from a halogen atom or a $(C_1$-$C_4)$alkyl, trifluoromethyl or $(C_1$-$C_4)$alkoxy group.

5. The compound according to claim 4 wherein $R_1$ is selected from ethyl, tertiobutyl and phenyl.

6. The compound according to claim 4 wherein $Ar_2$ is selected from the group consisting of phenyl, 2-methoxyphenyl, 2,6-dichlorophenyl, 3,5-dimethoxyphenyl, 3,4-dimethoxyphenyl, 2,6-dibromophenyl, 2-bromo-6-chlorophenyl, 2,4-dichlorophenyl and 3,5-dichlorophenyl.

7. A compound of the formula:

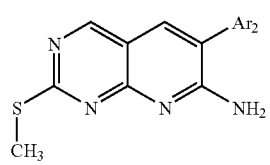

wherein $Ar_2$ represents a phenyl group which is unsubstituted or substituted 1 to 5 times with substituents independently selected from a halogen atom or a $(C_1-C_4)$alkyl, trifluoromethyl or $(C_1-C_4)$alkoxy group.

8. The compound according to claim 7 wherein $Ar_2$ is selected from the group consisting of phenyl, 2-methoxyphenyl, 2,6-dichlorophenyl, 3,5-dimethoxyphenyl, 3,4-dimethoxyphenyl, 2,6-dibromophenyl, 2-bromo-6-chlorophenyl, 2,4-dichlorophenyl and 3,5-dichlorophenyl.

* * * * *